US012239666B2

(12) United States Patent
Beg et al.

(10) Patent No.: US 12,239,666 B2
(45) Date of Patent: Mar. 4, 2025

(54) ONCOLYTIC VIRUS OR ANTIGEN PRESENTING CELL MEDIATED CANCER THERAPY USING TYPE I INTERFERON AND CD40-LIGAND

(71) Applicants: H. LEE MOFFITT CANCER CENTER AND RESEARCH INSTITUTE, INC., Tampa, FL (US); MEMGEN, INC., Houston, TX (US)

(72) Inventors: Amer A. Beg, Tampa, FL (US); Scott J. Antonia, Durham, NC (US); Mark J. Cantwell, Meadow Vista, CA (US)

(73) Assignees: H. LEE MOFFITT CANCER CENTER AND RESEARCH INSTITUTE, INC. INC., Tampa, FL (US); MEMGEN, INC., Houston, TX (US)

( * ) Notice: Subject to any disclaimer, the term of this patent is extended or adjusted under 35 U.S.C. 154(b) by 749 days.

(21) Appl. No.: 17/253,927

(22) PCT Filed: Jun. 18, 2019

(86) PCT No.: PCT/US2019/037753

§ 371 (c)(1),
(2) Date: Dec. 18, 2020

(87) PCT Pub. No.: WO2019/246111

PCT Pub. Date: Dec. 26, 2019

(65) Prior Publication Data

US 2021/0268090 A1 Sep. 2, 2021

Related U.S. Application Data

(60) Provisional application No. 62/687,076, filed on Jun. 19, 2018.

(51) Int. Cl.

| | |
|---|---|
| ***A61K 35/28*** | (2015.01) |
| ***A61K 35/761*** | (2015.01) |
| ***A61K 39/00*** | (2006.01) |
| ***A61P 35/00*** | (2006.01) |
| ***C07K 14/56*** | (2006.01) |
| ***C07K 14/705*** | (2006.01) |
| ***C12N 5/0784*** | (2010.01) |
| ***C12N 7/00*** | (2006.01) |

(52) U.S. Cl.
CPC ............ *A61K 35/28* (2013.01); *A61K 35/761* (2013.01); *A61K 39/4615* (2023.05); *A61K 39/4622* (2023.05); *A61K 39/464441* (2023.05); *A61K 39/464838* (2023.05); *A61P 35/00* (2018.01); *C07K 14/56* (2013.01); *C07K 14/70578* (2013.01); *C12N 5/0639* (2013.01); *C12N 7/00* (2013.01); *A61K 2039/5256* (2013.01); *A61K 2039/585* (2013.01); *A61K 2239/57* (2023.05); *C12N 2510/00* (2013.01); *C12N 2710/10321* (2013.01); *C12N 2710/10332* (2013.01); *C12N 2710/10343* (2013.01)

(58) Field of Classification Search
CPC ........... A61K 2039/585; A61K 35/761; A61K 39/001141; A61K 2039/5154; A61K 2039/55522; A61K 2039/55538; A61K 2039/55572; A61K 35/763; A61K 39/12; A61K 39/245; A61K 39/25; A61P 35/00; C07K 14/555; C07K 14/565; C07K 14/70578; C07K 14/71; C07K 14/4748; C07K 16/32; C07K 2319/00; C12N 2710/10332; C12N 2510/00; C12N 2710/10343; C12N 5/0639; C12N 2710/16733
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |

(Continued)

FOREIGN PATENT DOCUMENTS

| | | | |
|---|---|---|---|
| JP | 2006523688 | A | 10/2006 |
| JP | 2012516682 | A | 7/2012 |
| WO | 2018/098279 | | 5/2018 |

OTHER PUBLICATIONS

Derynck et al. Nature, 1980, vol. 285, pp. 542-547.*
Aurelian, L. "Oncolytic viruses as immunotherapy: progress and remaining challenges" Onco. Targets Ther., 2016; 9:2627-2637.
Bernhard, et al., "Generation of Immunostimulatory Dendritic Cells from Human CD34+ Hematopoietic Progenitor Cells of the Bone Marrow and Peripheral Blood", Cancer Research, 55:1099-104 (1995).
Caux, et al., "GM-CSF and TNF-α cooperate in the generation of dendritic Langerhans cells", Nature 360:258-61 (1992).

(Continued)

*Primary Examiner* — Bao Q Li
(74) *Attorney, Agent, or Firm* — Jackson Walker LLP; Leisa Talbert Peschel

(57) ABSTRACT

The invention concerns APCs, such as DCs, comprising a combination of an exogenous type I interferon and an exogenous CD40-L or one or more heterologous nucleic acid sequences encoding a combination of an exogenous type I IFN and an exogenous CD40-L, such as a combination of IFNβ and CD40-L; and methods for treating a malignancy by administering such APCs to a subject in need thereof. In certain embodiments, a subject is treated with an irradiation therapy before administering the APCs, such as DCs, of the invention. The invention also concerns an oncolytic virus comprising a combination of a type I IFN and CD40-L or one or more nucleic acid sequences encoding a combination of a type I IFN and CD40-L, such as a combination of IFNβ and CD40-L; and methods for treating a malignancy by administering such oncolytic virus to a subject in need thereof.

8 Claims, 13 Drawing Sheets

Specification includes a Sequence Listing.

(56) References Cited

U.S. PATENT DOCUMENTS

| | | | |
|---|---|---|---|
| 4,938,949 A | 7/1990 | Borch et al. | |
| 4,992,478 A | 2/1991 | Geria | |
| 5,851,756 A | 12/1998 | Steinman et al. | |
| 5,994,126 A | 11/1999 | Steinman et al. | |
| 7,495,090 B2 * | 2/2009 | Prussak ............ | C07K 14/70575 536/23.4 |
| 7,928,213 B2 | 4/2011 | Prussak et al. | |
| 8,138,310 B2 | 3/2012 | Prussak et al. | |
| 8,389,278 B2 | 3/2013 | Tjoa et al. | |
| 2003/0091564 A1 | 5/2003 | Armitage et al. | |
| 2003/0138405 A1 | 7/2003 | Fueyo et al. | |
| 2007/0071722 A1 | 3/2007 | Huang | |
| 2018/0169271 A1 | 6/2018 | Cantwell et al. | |
| 2021/0128653 A1 | 5/2021 | Cantwell et al. | |

OTHER PUBLICATIONS

Chiocca, et al., "Oncolytic Viruses and Their Application to Cancer Immunotherapy", 2014, Cancer Immunol Res. 2 (4):295-300.

Choi, et al., "From Benchtop to Bedside: A Review of Oncolytic Virotherapy", 2016, Biomedicines; 4(3):18, pp. 1-20.

Copolovici, et al., "Cell-Penetrating Peptides: Design, Synthesis, and Applications", ACS Nano, 2014, 8(3): pp. 1972-1994.

Freudenthal, et al., "The distinct surface of human blood dendritic cells, as observed after an improved isolation method", Proc. Natl. Acad. Sci. USA, 87:pp. 7698-7702, (1990).

Graham, et al., "Manipulation of Adenovirus Vectors", Methods Mol Biol, (1991), 7, pp. 109-128.

Ivics, et al., "Nonviral Gene Delivery with the Sleeping Beauty Transposon System", Hum Gene Therapy, 2011, 22(9): pp. 1043-1051.

Lawler, et al., "Oncolytic Viruses in Cancer Treatment: A Review", 2017, JAMA Oncology; 3(6): pp. 841-849.

Macatonia, et al., "Suppression of immune responses by dendritic cells infected with HIV", Immunology, (1989), 67: pp. 285-289.

Maffei, et al., "A novel closed system utilizing styrene copolymer bead adherence for the production of human dendritic cells", Transfusion, (2000), 40: pp. 1419-1420.

Markowicz, et al., "Granulocyte-macrophage colony-stimulating factor promotes differentiation and survival of human peripheral blood dendritic cells in vitro", J. Clin. Invest., (1990), 85: pp. 955-961.

Nemudryi, et al., "TALEN and CRISPR/Cas Genome Editing Systems: Tools of Discovery", Acta Naturae, Jul.-Sep. 2014, 6(3): pp. 19-40.

O'Doherty, et al., "Dendritic Cells Freshly Isolated from Human Blood Express CD4 and Mature into Typical Immunostimulatory Dendritic Cells after Culture in Monocyte-conditioned Medium", J. Exp. Med., (1993), 178: pp. 1067-1076.

Palucka, et al., "Cancer immunotherapy via dendritic cells", Nature Reviews Cancer, 2012, 12: pp. 265-277.

Racher, et al., "Culture of 293 cells in different culture systems: Cell growth and recombinant adenovirus production", Biotechnology Techniques, (1995), 9: pp. 169-174.

Russell, et. al., "Oncolytic Virotherapy", Nat. Biotechnol., (2012), 30(7):pp. 658-670.

Suzuki, et al., "The presence of the adenovirus E3 region improves the oncolytic potency of conditionally replicative adenoviruses", Clin. Cancer Res., Nov. 2002, 8(11): p. 3348-3359.

Tollefson, et al., "The E3-1 1.6-kDa Adenovirus Death Protein (ADP) Is Required for Efficient Cell Death: Characterization of Cells Infected with adp Mutants," Virology, (1996), 220: pp. 152-162.

Trabulo, et al., "Cell-Penetrating Peptides—Mechanisms of Cellular Uptake and Generation of Delivery Systems", Pharmaceuticals, (2010), 3: pp. 961-993.

Wagstaff, et al., "Protein Transduction: Cell Penetrating Peptides and Their Therapeutic Applications", Current Medicinal Chemistry, (2006), 13(12): pp. 1371-1387.

Young, et al., "Dendritic cells stimulate primary human cytolytic lymphocyte responses in the absence of CD4+ helper T cells", J. Exp. Med., (1990), 171: pp. 1315-1332.

Freytag et al., "Efficacy of oncolytic adenovirus expressing suicide genes and interleukin-12 in preclinical model of prostate cancer", Gene Therapy, vol. 20, (12), 2013, pp. 1-22.

Office Action mailed May 23, 2023 from the Japanese Patent Office for co-pending application No. JP 2020-570095, with English Translation, 15 pages.

* cited by examiner

ONCOLYTIC VIRUS OR ANTIGEN PRESENTING CELL MEDIATED CANCER THERAPY USING TYPE I INTERFERON AND CD40-LIGAND

CROSS-REFERENCE TO RELATED APPLICATIONS

This application is the National Stage of International Application Number PCT/US2019/037753, filed Jun. 18, 2019, which claims the benefit of the U.S. Provisional Application Ser. No. 62/687,076, filed Jun. 19, 2018, which is hereby incorporated by reference in its entirety.

GOVERNMENT SUPPORT

This invention was made with government support under Grant No. 5P50CA168536-03 awarded by the National Institutes of Health, NCI Skin Specialized Programs of Research Excellence. The government has certain rights in the invention.

The Sequence Listing for this application is labeled "2R00418.TXT" which was created on Dec. 17, 2020 and is 52 KB. The entire contents of the sequence listing is incorporated herein by reference in its entirety.

BACKGROUND OF THE INVENTION

Human tumors express a number of protein antigens that can be recognized by T lymphocytes (T cells), thus providing potential targets for cancer immunotherapy. The present invention relates generally to the field of cancer immunotherapy, cellular vaccines, virology, immunology, and medicine. More particularly, it concerns dendritic cell vaccines and oncolytic viral vectors for the treatment of cancer.

Dendritic cells (DCs) are antigen presenting cells (APCs) instrumental in the initiation of T cell-dependent immune responses. DC vaccines have shown promise for treating some cancers; however, only one agent is currently approved by the FDA, sipuleucel-T (PROVENGE®), for treating prostate cancer. Various cocktails of cytokines are used to activate DCs based on the rationale that vaccine cells alone lead to T cell activation. In reality, DCs represent diverse subsets with distinct functions. It is not clear whether a DC vaccine can be sufficient to induce robust T cell activation. In addition, pre-clinical studies have shown that different DC subsets have distinct functions, e.g. in the transportation of tumor antigens to draining lymph nodes, versus T cell activation in lymph nodes.

Oncolytic viruses are a class of cancer therapeutic agents having one or both of the following mechanisms of action: 1) tumor cell killing through selective viral replication in tumor cells resulting in direct tumor lysis and 2) induction of systemic anti-tumor immunity by releasing antigens from destroyed tumor cells. The FDA approved its first oncolytic virus in 2015, talimogene laherparepvec (IMLYGIC®), a genetically modified oncolytic herpes virus encoding granulocyte-macrophage colony-stimulating factor (GM-CSF) for the local treatment of melanoma.

BRIEF SUMMARY OF THE INVENTION

Certain embodiments of the invention provide an APC, such as a DC, expressing a combination of an exogenous type I IFN and an exogenous CD40-ligand (CD40-L, also known as CD154), such as a combination of an exogenous IFNβ and an exogenous CD40-ligand (CD40-L), for example via one or more heterologous nucleic acid sequences encoding a combination of an exogenous IFNβ and an exogenous CD40-L.

Another embodiment of the invention provides an oncolytic virus expressing a combination of type I IFN and CD40-L, for example, via one or more heterologous nucleic acid sequences encoding a combination of IFNβ and CD40-L.

A preferred embodiment of the invention provides an oncolytic adenovirus expressing a combination of type I IFN and CD40-L, for example, via one or more heterologous nucleic acid sequences encoding a combination of IFNβ and CD40-L.

Further embodiments of the invention provide methods of treating a malignancy in a subject by administering an APC, such as a DC, or an oncolytic virus disclosed herein, and optionally in combination by administering a checkpoint inhibitor to the subject. When APCs, such as DCs, of the invention are administered to a subject, an irradiation therapy is also administered to the subject before administering the APCs or DCs.

Oncolytic virus expressing a combination of type I IFN and CD40-L, such as a combination of IFNβ and CD40-L, can be administered without an irradiation therapy. However, administering an oncolytic virus disclosed herein can be combined by administering a checkpoint inhibitor.

In preferred embodiments, a subject suffering from a malignancy is refractory to a therapy with a checkpoint inhibitor.

BRIEF DESCRIPTION OF THE SEQUENCES

Figure 1:
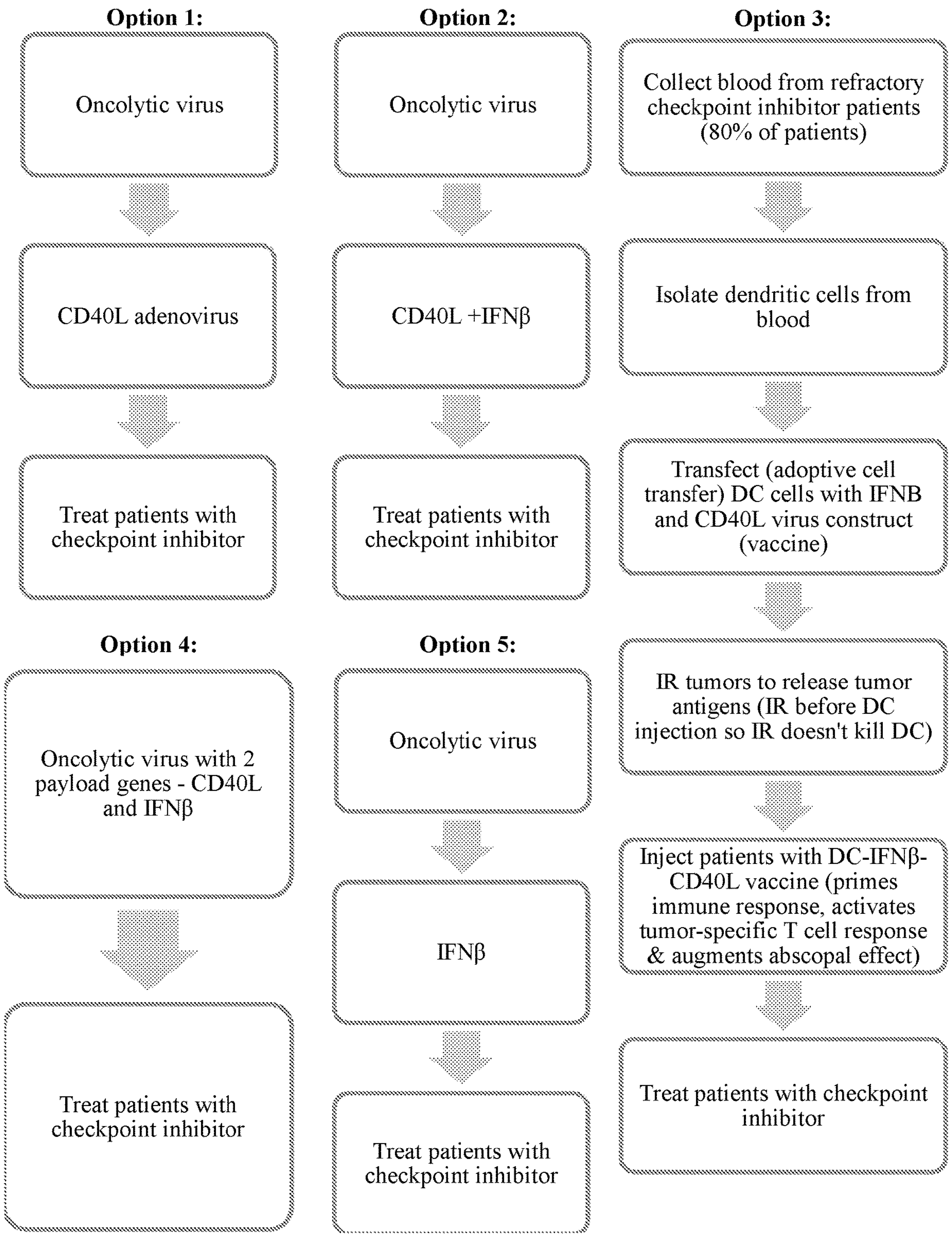
FIG. 1 shows a schematic of embodiments of methods of treating a malignancy according to the invention. Reference to "IFNβ" in FIG. 1 is intended to be representative of any type I IFN. Furthermore, reference to "dendritic cells" or "DC" in FIG. 1 is intended to be representative of any APC.

```
SEQ ID NO: 1 is the amino acid sequence of the
human wild-type interferon-α
(UniProtKB Reference No. P05014):
MALSFSLLMAVLVLSYKSICSLGCDLPQTHSLGNRRALILLAQMGRISH
FSCLKDRHDFGFPEEEFDGHQFQKAQAISVLHEMIQQTFNLFSTEDSSA
AWEQSLLEKFSTELYQQLNDLEACVIQEVGVEETPLMNEDSILAVRKYF
QRITLYLTEKKYSPCAWEVVRAE IMRSLSFSTN LQKRLRRKD

SEQ ID NO: 2 is the amino acid sequence of the
human wild-type interferon-β
(UniProtKB Reference No. P01574):
MTNKCLLQIALLLCFSTTALSMSYNLLGFLQRSSNFQCQKLLWQLNGRL
EYCLKDRMNFDIPEEIKQLQQFQKEDAALTIYEMLQNIFAIFRQDSSST
GWNETIVENLLANVYHQINHLKTVLEEKLEKEDFTRGKLMSSLHLKRYY
GRILHYLKAKEYSHCAWTIVR VEILRNFYFINRLTGYLRN
```

-continued

```
SEQ ID NO: 3 is the amino acid sequence of the
human wild-type interferon-ε
(UniProtKB Reference No. Q86WN2):
MIIKHFFGTVLVLLASTTIFSLDLKLIIFQQRQVNQESLKLLNKLQTLS
IQQCLPHRKNFLLPQKSLSPQQYQKGHTLAILHEMLQQIFSLFRANISL
DGWEENHTEKFLIQLHQQLEYLEALMGLEAEKLSGTLGSDNLRLQVKMY
FRRIHDYLENQDYSTCAWAIVQVEISRCLFFVFSLTEKLSKQGRPLNDM
KQELTTEFRSPR

SEQ ID NO: 4 is the amino acid sequence of the
human wild-type interferon-κ
(UniProtKB Reference No. Q9P0W0):
MSTKPDMIQKCLWLEILMGIFIAGTLSLDCNLLNVHLRRVTWQNLRHLS
SMSNSFPVECLRENIAFELPQEFLQYTQPMKRDIKKAFYEMSLQAFNIF
SQHTFKYWKERHLKQIQIGLDQQAEYLNQCLEEDKNENEDMKEMKENEM
KPSEARVPQLSSLELRRYFHRIDNFLKEKKYSDCAWEIVRVEIRRCLYY
FYKFTALFRRK

SEQ ID NO: 5 is the amino acid sequence of the
human wild-type interferon-ω
(UniProtKB Reference No. P05000):
MALLFPLLAALVMTSYSPVGSLGCDLPQNHGLLSRNTLVLLHQMRRISP
FLCLKDRRDFRFPQEMVKGSQLQKAHVMSVLHEMLQQIFSLFHTERSSA
AWNMTLLDQLHTGLHQQLQHLETCLLQVVGEGESAGAISSPALTLRRYF
QGIRVYLKEKKYSDCAWEVVRMEIMKSLFLSTNMQERLRSKDRDLGSS

SEQ ID NO: 6 is the amino acid sequence of the
human CD40-L
(UniProtKB Reference No. P29965):
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKENSFEMQKGDQNPQIAAHVISEASSKTTSVLQWAEKGYYT
MSNNLVTLENGKQLTVKRQGLYYIYAQVTFCSNREASSQAPFIASLCLK
SPGRFERILLRAANTHSSAKPCGQQSIHLGGVFELQPGASVFVNVTDPS
QVSHGTGFTSFGLLKL
```

SEQ ID NOS: 7-18 are examples of chimeric CD40-L amino acid sequences.

SEQ ID NOS: 19-23 are nucleic acid sequences encoding chimeric human/mouse CD40-L.

SEQ ID NO: 24 is a nucleic acid sequence encoding the chimeric human/mouse CD40-L MEM40.

SEQ ID NOS: 25-30 are nucleic acid sequences encoding chimeric human/mouse CD40-L.

DETAILED DESCRIPTION OF THE INVENTION

The invention provides that a combination of Type 1 IFN and CD40-L can activate the function of APCs, such as DCs, to promote T cell activation. In particular, a combination of Type I IFN and CD40-L can enhance the cross-priming function of APC, such as DC to activate CD8 T cells. Therefore, stable expression of a combination of type I IFN, such as, IFN-α, (or any subtype of IFN-α, such as subtype α1, α2, α4, α5, α6, α7, α8, α10, α13, α14, α16, α17, or α21), IFN-β, IFN-ε, IFN-κ, and IFN-ω, and a CD40-L in APCs, such as DCs, would enhance intrinsic functionality of APCs or DCs and also produce a vaccine capable of potent activation of endogenous DCs, thereby enhancing the ability of endogenous DCs to activate T cells.

As used herein, the term "antigen presenting cell" (APC) refers to professional antigen presenting cell, which is selected from among dendritic cells, macrophages, and B cells. In some embodiments, the APC is a DC. In some embodiments, the APC is a mammalian cell. In some embodiments, the APC, such as DC, macrophage, or B cell is a human cell.

Accordingly, certain embodiments of the invention provide APCs, such as, DCs, expressing a combination of a type I IFN, such as IFNβ, and CD40-L, for example, via one or more heterologous nucleic acid sequences encoding an exogenous IFNβ and an exogenous CD40-L. Such APC, particular DC, vaccine would induce a potent systemic T cell response when coupled with a cell death inducing treatment. In certain embodiments, the APC, such as DC, comprises a replication deficient virus.

In certain embodiments, the invention provides a DC vaccine comprising a DC with a viral vector, such as a lentivirus, that expresses a combination of IFNβ and CD40-L.

Additional embodiments of the invention provide oncolytic viruses expressing a combination of a type I IFN, such as, IFN-α, IFN-β, IFN-ε, IFN-κ, and IFN-ω, and CD40-L, for example, via one or more heterologous nucleic acid sequences encoding a combination of IFNβ and CD40-L. Any oncolytic virus may be utilized. In some embodiments, the oncolytic virus can be adenovirus, reovirus, herpes virus, picornavirus (including coxsackievirus, poliovirus, and Seneca Valley virus), paramyxovirus (including measles virus and Newcastle disease virus (NDV)), parvovirus, rhabdovirus (including vesicular stomatitis virus (VSV)), or vaccinia virus. Preferably, the oncolytic virus is replication competent.

Further embodiments of the invention provide methods of treating a malignancy in a subject by administering the APCs, such as DCs, or oncolytic viruses disclosed herein, in combination by administering a checkpoint inhibitor to the subject. When APCs, such as DCs, of the invention are administered to a subject, an irradiation therapy is administered to the subject before administering the APCs or DCs. FIG. 1 shows a schematic of embodiments of methods of treating a malignancy according to the invention (Options 1-5).

IFNα can be a human IFNα represented by the sequence of SEQ ID NO: 1. IFNα can be a mammalian IFNα, such as, mouse, rat, rabbit, pig, feline, canine, or bovine IFNα. Additional embodiments of IFNα from other mammals are known to a skilled artisan and such embodiments are within the purview of the invention. In certain embodiments, IFNα has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNα, for example, IFNα of SEQ ID NO: 1.

IFNβ can be a human IFNβ represented by the sequence of SEQ ID NO: 2. IFNβ can be a mammalian IFNβ, such as, mouse, rat, rabbit, pig, feline, canine, or bovine IFNβ. Additional embodiments of IFNβ from other mammals are known to a skilled artisan and such embodiments are within the purview of the invention. In certain embodiments, IFNβ has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNβ, for example, IFNβ of SEQ ID NO: 2. In a specific embodiment, IFNβ lacks the first 22 amino acids of SEQ ID NO: 2 and optionally, further has a substitution of cysteine 17 of the resultant 165 amino acid peptide with serine.

IFNε can be a human IFNε represented by the sequence of SEQ ID NO: 3. IFNε can be a mammalian IFNε, such as, mouse, rat, rabbit, pig, feline, canine, or bovine IFNε. Additional embodiments of IFNε from other mammals are known to a skilled artisan and such embodiments are within the purview of the invention. In certain embodiments, IFNε has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNε, for example, IFNε of SEQ ID NO: 3.

IFNκ can be a human IFNκ represented by the sequence of SEQ ID NO: 4. IFNκ can be a mammalian IFNκ, such as, mouse, rat, rabbit, pig, feline, canine, or bovine IFNκ. Additional embodiments of IFNκ from other mammals are known to a skilled artisan and such embodiments are within the purview of the invention. In certain embodiments, IFNκ has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNκ, for example, IFNκ of SEQ ID NO: 4.

IFNω can be a human IFNω represented by the sequence of SEQ ID NO: 5. IFNω can be a mammalian IFNω, such as, mouse, rat, rabbit, pig, feline, canine, or bovine IFNω. Additional embodiments of IFNω from other mammals are known to a skilled artisan and such embodiments are within the purview of the invention. In certain embodiments, IFNω has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNω, for example, IFNω of SEQ ID NO: 5.

CD40-L can be a human CD40-L represented by the sequence of SEQ ID NO: 6. CD40-L can be a mammalian CD40-L, such as, mouse, rat, rabbit, pig, feline, canine, or bovine CD40-L. Additional embodiments of CD40-L from other mammals are known to a skilled artisan and such embodiments are within the purview of the invention. In certain embodiments, CD40-L has between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type CD40-L, for example, CD40-L of SEQ ID NO: 6.

The CD40-L can be a chimeric CD40-L or a non-chimeric CD40-L polypeptide. In some embodiments, the CD40-L expressed in an APC, such as a DC, or an oncolytic virus of the invention, is a chimeric CD40-L. Such chimeric CD40-L polypeptides comprise CD40-L domains or subdomains from at least two different species, for example, human and mouse CD40-L. A chimeric CD40-L provides higher stimulation of the immune response compared to a naturally occurring CD40-L. Examples of chimeric CD40-L suitable for use in the current invention are disclosed in U.S. Pat. Nos. 7,495,090, 7,928,213, and 8,138,310. Each of these patents is incorporated herein by reference in their entirety.

In certain embodiments of chimeric CD40-L, at least one domain or subdomain of CD40-L that contains a cleavage site of human CD40-L is replaced with a corresponding domain or subdomain of non-human CD40-L, preferably murine CD40-L. In addition, a chimeric CD40-L can comprise a domain or subdomain of human CD40-L that binds to a CD40-L receptor. Domains I to IV of a human CD40-L (SEQ ID NO: 6) correspond to amino acid portions 1-14, 14-45, 46-110, and 111-261 of SEQ ID NO: 6. A skilled artisan can determine domains I to IV of a non-human CD40-L based on sequence alignment of the non-human CD40-L with the human CD40-L. Certain domain positions of non-human CD40-L are provided in Table 1 of U.S. Pat. No. 7,495,090, which is herein incorporated by reference in its entirety.

In some embodiments, the chimeric CD40-L comprises a first subdomain of non-human CD40-L, wherein the subdomain replaces a cleavage site of human CD40-L, and a second subdomain of human CD40-L that binds to a CD40-L receptor.

The first subdomain can comprise a subdomain of domain IV of a non-human CD40-L. In addition, the first subdomain can further comprise domain III, or a subdomain or domain III, of a non-human CD40-L. In certain embodiments, the first subdomain replaces a portion of a cleavage site of human CD40-L. In further embodiments, in addition to domain IV or a subdomain of domain IV, and optionally, domain III or a subdomain of domain III, a chimeric CD40-L further comprises domain II or a subdomain of domain II, of a non-human CD40-L. Furthermore, the first subdomain of a chimeric CD40-L can comprise domain I or a subdomain or domain I, of non-human CD40-L. Thus, in certain chimeric CD40-L, the first subdomain comprises domains or subdomains of domain I, II, III and IV, of a non-human CD40-L. In preferred embodiments, the non-human CD40-L is a murine CD40-L.

In preferred embodiments, the chimeric human/mouse CD40 ligand has 92% amino acid sequence homology with human CD40L (SEQ ID NO: 12) (See, U.S. Pat. No. 7,495,090, herein incorporated by reference and referred to herein as "MEM40"). "CD40 ligand" and "CD40-L" may be used interchangeably herein, and may also be referred to as "CD154". Specifically, domains I, II and III—the regions that contain the intracellular, intra-membrane, and proximal extracellular domains, respectively, of this molecule—have been fully humanized. In domain IV, which contains the CD40 binding portion of the molecule, only those murine domains necessary for optimum CD40 ligand expression in cells are retained. MEM40 is fully humanized at the 3' end of the molecule where antibody binding neutralizes the activity of the murine CD154 (CD40 ligand) when administered to humans.

Non-limiting examples of chimeric CD40-L useful in the current invention comprise the following sequences:

SEQ ID NO: 7
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREPSSQRPFIVGLWLKP
SSGSERILLKAANTHSSSQLCEQQSVHLGGVFELQPGASVFVNVTDPSQ
VSHGTGFTSFGLLKL

SEQ ID NO: 8:
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE
NGKQLTVKRQGLYYIYAQVTFCSNREPSSQRPFIVGLWLKPSSGSERIL
LKAANTHSSSQLCEQQSVHLGGVFELQPGASVFVNVTDPSQVSHGTGFT
SFGLLKL

SEQ ID NO: 9:
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREASSQAPFIVGLWLKP
SSGSERILLKAANTHSSSQLCEQQSVHLGGVFELQPGASVFVNVTDPSQ
VSHGTGFTSFGLLKL

SEQ ID NO: 10
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE
NGKQLTVKRQGLYYIYAQVTFCSNREASSQAPFIVGLWLKPSSGSERIL
LKAANTHSSSQLCEQQSVHLGGVFELQPGASVFVNVTDPSQVSHGTGFT
SFGLLKL

SEQ ID NO: 11
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREASSQAPFIVGLWLKP
SSGSERILLKAANTHSSSQLCEQQSIHLGGVFELQPGASVFVNVTDPSQ
VSHGTGFTSFGLLKL

SEQ ID NO: 12
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE

-continued
NGKQLTVKRQGLYYIYAQVTFCSNREASSQAPFIVGLWLKPSSGSERIL
LKAANTHSSSQLCEQQSIHLGGVFELQPGASVFVNVTDPSQVSHGTGFT
SFGLLKL SEQ ID NO: 13
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREASSQAPFIVGLWLKP
SSGSERILLKAANTHSSAKPCGQQSIHLGGVFELQPGASCFVNVTDPSQ
VSHGTGFTSFGLLKL SEQ ID NO: 14
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE
NGKQLTVKRQGLYYIYAQVTFCSNREASSQAPFIVGLWLKPSSGSERIL
LKAANTHSSAKPCGQQSIHLGGVFELQPGASVFVNVTDPSQVSHGTGFT
SFGLLKL SEQ ID NO: 15
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREPSSQRPFIVGLWLKP
SSGSERILLKAANTHSSSQLCEQQSIHLGGVFELQPGASVFVNVTDPSQ
VSHGTGFTSFGLLKL SEQ ID NO: 16
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE
NGKQLTVKRQGLYYIYAQVTFCSNREPSSQRPFIVGLWLKPSSGSERIL
LKAANTHSSSQLCEQQSIHLGGVFELQPGASVFVNVTDPSQVSHGTGFT
SFGLLKL SEQ ID NO: 17
MIETYSQPSPRSVATGLPASMKIFMYLLTVFLITQMIGSVLFAVYLHRR
LDKVEEEVNLHEDFVFIKKLKRCNKGEGSLSLLNCEEMRRQFEDLVKDI
TLNKEEKKENSFEMQRGDEDPQIAAHVVSEANSNAASVLQWAKKGYYTM
KSNLVTLENGKQLTVKRQGLYYIYAQVTFCSNREPSSQRPFIVGLWLKP
SSGSERILLKAANTHSSAKPCGQQSIHLGGVFELQPGASVFVNVTDPSQ
VSHGTGFTSFGLLKL SEQ ID NO: 18
MIETYNQTSPRSAATGLPISMKIFMYLLTVFLITQMIGSALFAVYLHRR
LDKIEDERNLHEDFVFMKTIQRCNTGERSLSLLNCEEIKSQFEGFVKDI
MLNKEETKKDEDPQIAAHVVSEANSNAASVLQWAKKGYYTMKSNLVTLE
NGKQLTVKRQGLYYIYAQVTFCSNREPSSQRPFIVGLWLKPSSGSERIL
LKAANTHSSAKPCGQQSIHLGGVFELQPGASVFVNVTDPSQVSHGTGFT
SFGLLKL Certain nucleotide sequences encoding the chimeric CD40-L of SEQ ID NOs: 7 to 18 are disclosed in U.S. Pat. Nos. 7,495,090, 7,928,213, and 8,138,310. These nucleotide sequences are incorporated herein by reference and use of such nucleotide sequences is envisioned herein.

The APCs or oncolytic viruses of the invention can comprise a nucleic acid encoding IFNα, wherein the IFNα comprises the human wild-type IFNα (SEQ ID NO:1) or a IFNα having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNα, for example, IFNα of SEQ ID NO: 1.

The APCs or oncolytic viruses of the invention can comprise a nucleic acid encoding IFNβ, wherein the IFNβ comprises the human wild-type IFNβ (SEQ ID NO: 2) or a IFNβ having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNβ, for example, IFNβ of SEQ ID NO: 2. In a specific embodiment, the nucleotide sequence encodes for a IFNβ that lacks the first 22 amino acids of SEQ ID NO: 2 and optionally, further has a substitution of cysteine 17 of the resultant 165 amino acid peptide with serine.

The APCs or oncolytic viruses of the invention can comprise a nucleic acid encoding IFNε, wherein the IFNε comprises the human wild-type IFNε (SEQ ID NO: 3) or a IFNε having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNε, for example, IFNε of SEQ ID NO: 3.

The APCs or oncolytic viruses of the invention can comprise a nucleic acid encoding IFNκ, wherein the IFNκ comprises the human wild-type IFNκ (SEQ ID NO: 4) or a IFNκ having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNκ, for example, IFNκ of SEQ ID NO: 4.

The APCs or oncolytic viruses of the invention can comprise a nucleic acid encoding IFNω, wherein the IFNω comprises the human wild-type IFNω (SEQ ID NO: 5) or a IFNω having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type IFNω, for example, IFNω of SEQ ID NO: 5.

The APCs or oncolytic viruses of the invention can comprise a nucleic acid encoding CD40-L, wherein the CD40-L comprises the human wild-type CD40-L (SEQ ID NO:6) or a CD40-L having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to the human wild-type CD40-L, for example, CD40-L of SEQ ID NO: 6. The APCs or oncolytic viruses of the invention can also comprise a nucleic acid encoding a chimeric CD40-L, wherein the chimeric CD40-L has a sequence selected from SEQ ID NOs: 7 to 18 or a CD40-L having between 80.00% and, up to, including 99.99% (e.g., 80, 81, 82, 83, 84, 85, 86, 87, 88, 89, 90, 91, 92, 93, 94, 95, 96, 97, 98, or 99%) sequence identity to a chimeric CD40-L having a sequence selected from SEQ ID NOs: 7 to 18.

In preferred embodiments, the APCs or oncolytic virus of the invention can comprise a nucleic acid encoding MEM40. For example, in preferred embodiments, the APCs or the oncolytic viruses of the invention comprise IFNβ comprising at least 80% sequence identity to the human IFNβ (SEQ ID NO: 2) and the CD40-L comprises at least 80% sequence identity to a chimeric CD40-L having a sequence of SEQ ID NO: 12.

One or more heterologous nucleic acid sequences encoding the combination of type I IFN and CD40-L can be in one or more viral constructs. Non-limiting examples of the viral constructs include an adenoviral construct, adeno-associated viral construct (AAV), poxvirus construct, lentiviral construct, alphaviral construct, herpesviral construct, retroviral construct, vaccinia viral construct, vesicular stomatitis viral construct, or herpes simplex viral construct.

In addition to nucleic acids encoding a type I interferon (e.g., IFNβ) and CD40-L (chimeric human/mouse CD40L), the oncolytic virus in accordance with the present invention can further include other modifications in its genome. For example, it can comprise additional DNA inserted into an already inactivated gene, or substituted for a deleted gene. The oncolytic virus may also have incorporated therein one or more promoters that impart to the virus an enhanced level of tumor cell specificity. In this way, the oncolytic virus may be targeted to specific cancer types using cancer cell-specific promoters. The term "tumor cell-specific promoter" or "tumor cell-specific transcriptional regulatory sequence" or "tumor-specific promoter" or "tumor-specific transcriptional regulatory sequence" indicates a transcriptional regulatory sequence, promoter and/or enhancer that is present at a higher level in the target cancer cell than in a normal cell. For example, the oncolytic virus for use in the invention may be under the control of an exogenously added regulator.

In preferred embodiments, the oncolytic virus is an adenovirus (Ad). Ad is a large (approximately 36 kb) DNA virus that infects humans, but which also display a broad host range. Physically, adenovirus is an icosahedral virus containing a double-stranded, linear DNA genome. There are approximately 50 serotypes of human adenoviruses, which are divided into six families based on molecular, immunological, and functional criteria. By adulthood, virtually every human has been infected with the more common adenovirus serotypes, the major effect being cold-like symptoms.

Adenoviral infection of host cells results in adenoviral DNA being maintained episomally, which reduces the potential genotoxicity associated with integrating vectors. In addition, adenoviruses are structurally stable, and no genome rearrangement has been detected after extensive amplification. Adenovirus can infect most epithelial cells regardless of their cell cycle stage. So far, adenoviral infection appears to be linked only to mild disease such as acute respiratory disease in humans.

The infectious cycle of the adenovirus takes place in 2 steps: the early phase which precedes initiation of the replication of the adenoviral genome, and which permits production of the regulatory proteins and proteins involved in the replication and transcription of the viral DNA, and the late phase which leads to the synthesis of the structural proteins. The early genes are distributed in 4 regions that are dispersed in the adenoviral genome, designated E1 to E4 ("E" denotes "early"). The early regions comprise at least six transcription units, each of which possesses its own promoter. The expression of the early genes is itself regulated, some genes being expressed before others. Three regions, E1, E2, and E4 are essential to replication of the virus. Thus, if an adenovirus is defective for one of these functions this protein will have to be supplied in trans, or the virus cannot replicate.

The E1 early region is located at the 5' end of the adenoviral genome, and contains 2 viral transcription units, E1A and E1B. This region encodes proteins that participate very early in the viral cycle and are essential to the expression of almost all the other genes of the adenovirus. In particular, the E1A transcription unit codes for a protein that transactivates the transcription of the other viral genes, inducing transcription from the promoters of the E1B, E2A, E2B, E3, and E4 regions and the late genes.

The adenovirus enters the permissive host cell via a cell surface receptor, and it is then internalized. The viral DNA associated with certain viral proteins needed for the first steps of the replication cycle enters the nucleus of the infected cells, where transcription is initiated. Replication of the adenoviral DNA takes place in the nucleus of the infected cells and does not require cell replication. New viral particles or virions are assembled after which they are released from the infected cells, and can infect other permissive cells.

The adenovirus is an attractive delivery system. Embodiments of the disclosure can utilize manufacturing process that can be free of or essentially free of protein, serum, and animal derived components making it suitable for a broad range of both prophylactic and therapeutic vaccine products.

If an adenovirus has been mutated so that it is conditionally replicative (replication-competent under certain conditions), a helper cell may be required for viral replication. When required, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, for example Vero cells or other monkey embryonic mesenchymal or epithelial cells. In certain aspects a helper cell line is 293. Various methods of culturing host and helper cells may be found in the art, for example (Racher, A. J., Fooks, A. R. & Griffiths, J. B. Biotechnol Tech (1995) 9: 169.)

Adenoviruses can be isolated using different methodologies. Most often, after transfection of the Ad genome, adenoviral plaques are isolated from the agarose overlaid cells and the viral particles are expanded for analysis. For detailed protocols the skilled artisan is referred to (Graham, F. L., and Prevec, L. (1991). Manipulation of adenovirus vectors. Methods Mol Biol 7, 109-128.).

Alternative technologies for the generation of adenovirus vectors include utilization of the bacterial artificial chromosome (BAC) system, in vivo bacterial recombination in a recA+ bacterial strain utilizing two plasmids containing complementary adenoviral sequences, and the yeast artificial chromosome (YAC) system (PCT publications 95/27071 and 96/33280, which are incorporated herein by reference).

There are a broad range of oncolytic virus types in development as anti-cancer agents, including adenovirus (see Russell et. al., 2012 Nat. Biotechnol.; 30(7):658-670; Lawler et. al., 2017 JAMA Oncology; 3(6):841-849; Choi et al., 2016, Biomedicines; 4(3):18; and Chiocca and Rabkin, 2014 Cancer Immunol Res. 2(4):295-300, which are incorporated herein by reference in their entirety).

Multiple biologic properties may be considered in selection or design of a therapeutic oncolytic adenovirus for desired therapeutic activity, including: selective targeting of cancer cells for infection through natural tropism of cell surface proteins or by engineering adenovirus to directly target cancer cells; selective replication in cancer cells; attenuation of viral pathogenesis; enhancing lytic activity; modification of the antiviral immune response that can lead to rapid clearance of adenovirus; and modification of systemic anti-tumor immunity through genetic modification of adenoviruses to incorporate cytokines, immune agonists, or immune checkpoint blockers.

Replication competent oncolytic adenovirus vectors have several properties that make them ideal for therapeutic applications, including infectivity of a broad range of cell and tumor types, infection of non-non-dividing cells, lack of genomic integration, high titers, capacity to carry transgenes, in vitro and in vivo stability, and high levels of expression of transgenes. Adenovirus expression vectors include constructs containing adenovirus sequences sufficient to (a) support packaging of the construct and (b) to ultimately express a recombinant gene construct that has been cloned therein.

Modulation of the biological properties of oncolytic adenoviruses can impact a range of immune interactions that may be beneficial or detrimental in effect on cancer treatment. The interactions depend on the specific tumor, the site and extent of the disease, the immunosuppressive tumor microenvironment, the oncolytic virus platform, the dose, time, and delivery conditions, as well as individual patient responses (see generally Aurelian L. "Oncolytic viruses as immunotherapy: progress and remaining challenges" Onco. Targets Ther. 2016; 9:2627-2637). For example, the presence of adenovirus E3 genes has been reported to increase the oncolytic potency of conditionally replicating adenovirus in vitro and in vivo (see Suzuki K, Alemany R, Yamamoto M, and Curiel D T "The presence of the adenovirus E3 region improves the oncolytic potency of conditionally replicative adenoviruses" Clin. Cancer Res. 2002 November; 8(11):3348-59). In particular, the E3-11.6 kDa Adenovirus Death Protein (ADP) is thought to be required for efficient cell death (see Tollefson A, Ryerse J, and Scaria A, et al. "The E3-11.6-kDa Adenovirus Death Protein (ADP) is required for efficient cell death: characterization of cells infected with adp mutants," Virology 1996; 220:152-162). However, for immunotherapeutic approaches to the treatment of cancer, it may be important to balance rapid cell death with sufficient expression of immune modulatory proteins for optimal induction of anti-cancer immune responses. The present disclosure provides such oncolytic adenoviruses.

Members of any of the 57 human adenovirus serotypes (HAdV-1 to 57) may incorporate heterologous nucleic acid encoding exogenous molecules, for example exogenous type I IFN and an exogenous CD40-ligand as disclosed herein. Human Ad5 is well characterized genetically and biochemically (GenBank M73260; AC 000008). Thus, in a particular embodiment, the oncolytic adenovirus is a replication competent Ad5 serotype or a hybrid serotype comprising an Ad5 component. The adenovirus may be a wild type strain but may be genetically modified to enhance tumor selectivity, for example by attenuating the ability of the virus to replicate within normal quiescent cells without affecting the ability of the virus to replicate in tumor cells. Non-limiting examples of replication competent oncolytic adenoviruses encompassed by the present disclosure include Delta-24, Delta-24-RGD, ICOVIR-5, ICOVIR-7, ONYX-015, ColoAd1, H101 and AD5/3-D24-GMCSF. Onyx-015 is a hybrid of virus serotype Ad2 and Ad5 with deletions in the E1B-55K and E3B regions to enhance cancer selectivity. H101 is a modified version of Onyx-015. ICOVIR-5 and ICOVIR-7 comprise an Rb-binding site deletion of E1A and a replacement of the E1A promoter by an E2F promoter. ColoAd1 is a chimeric Add11p/Ad3 serotype. AD5/3-D24-GMCSF (CGTG-102) is a serotype 5/3 capsid-modified adenovirus encoding GM-CSF (the Ad5 capsid protein knob is replaced with a knob domain from serotype 3).

Oncolytic adenoviruses injected into a tumor induce cell death and release of new adenovirus progeny that, by infecting the neighbor cells, generates a treatment wave that, if not halted, may lead to the total destruction of the tumor.

Within some embodiments of the disclosure, a combination of heterologous sequences encoding Type I IFN and CD40-L can be incorporated into nonessential region(s) of the adenovirus. In a preferred embodiment of the disclosure, the adenovirus contains a 24 nucleotide deletion in E1, deletion of the E1B-55K region, and deletion of E3B regions to enhance cancer selectivity Viral regions may be altered for multiple purposes to impart desirable therapeutic properties. Non-limiting examples of therapeutic properties may include enhanced viral replication and spread, enhanced oncolysis, preferential targeting of tumor cells versus normal cells, enhanced immune activation, and protection of virus from the host immune system. Viral regions for the purposes described above may be either eliminated (complete or partial deletions), made non-functional, modified to attenuate function, or substituted by other sequences. Oncolytic viruses may also be altered to include one or more heterologous genes encoding therapeutic protein(s) and/or immunomodulatory protein(s). In a particular embodiment, an oncolytic virus modified to express a combination of IFNβ and CD40-L.

Optionally, signal peptides, or nucleic acids encoding them, may be employed for surface localization of a desired polypeptide.

In preferred embodiments, the APC, such as DC, is a human APC or DC. Preferably, APCs, such as DCs, from a human subject having a malignancy are isolated and genetically modified to express a combination of an exogenous type I IFN and an exogenous CD40-L, for example via one or more heterologous nucleic acid sequences encoding a combination of IFNβ and CD40-L. In preferred embodiments, the CD40-L is MEM40.

The oncolytic virus may be genetically modified further to improve one or more properties for use in treatment of cancer, including, selective replication in cancer cells; attenuation of viral pathogenesis; enhancing lytic activity; modification of the antiviral immune response that can lead to rapid clearance of virus; and modification of viral-induced systemic anti-tumor immunity.

In embodiments wherein the oncolytic virus has an RNA genome, the genes encoding the type I IFN and CD40-L may be rendered suitable for expression from an RNA viral genome prior to insertion of the gene into the genome. For example, the gene encoding the type I IFN and CD40-L may undergo replacement of thymine with uracil to facilitate expression from an RNA viral genome. Other modifications that may be suitable for such embodiments will be known to the person of ordinary skill in the art.

Expression cassettes included in vectors useful in the present disclosure contain (in a 5'-to-3' direction) a transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery gathers and integrates the regulatory information conveyed by each element, allowing different genes to evolve distinct, often complex patterns of transcriptional regulation. A promoter used in the context of the present disclosure includes constitutive, inducible, and tissue-specific promoters.

Type I IFN and CD40-L nucleic acids expression may be under the control of a promoter functional in mammalian cells, such as human tumor cells. In one embodiment, the promoters directing expression of a Type I IFN and CD40-L are an SV promoter and cytomegalovirus (CMV) promoter, respectively.

The expression constructs provided herein may comprise a promoter to drive expression of the programming genes. A promoter generally comprises a sequence that functions to position the start site for RNA synthesis. The best example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. These are typically in the region 30 to 110 bp upstream of the start site, although promoters have been shown to contain functional elements downstream of the start site as well. To bring a coding sequence "under the control of" a promoter, one positions the 5-prime end of the transcription initiation site of the transcriptional reading frame "downstream" of (i.e., 3-prime of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be naturally associated with a nucleic acid sequence and obtained by isolating the 5-prime non-coding sequences located upstream of the coding segment and/or exon. Such a promoter can be referred to as "endogenous." Similarly, an enhancer may be naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression.

One can employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high-level expression of the introduced DNA segment, such as is advantageous in the large-scale production of recombinant proteins and/or peptides. The promoter may be heterologous or endogenous.

Non-limiting examples of promoters include early or late viral promoters, such as SV40 early or late promoters, cytomegalovirus (CMV) immediate early promoters, Rous Sarcoma Virus (RSV) early promoters, and eukaryotic cell promoters.

A specific initiation signal may also be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would be readily capable of providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements can bypass the ribosome scanning model of 5-prime methylated Cap dependent translation and begin translation at internal sites (Pelletier et. al. 1988 Molecular and Cellular Biology). IRES elements from two members of the picornavirus family (polio and encephalomyocarditis) have been described (Pelletier et. al. 1988 Molecular and Cellular Biology), as well an IRES from a mammalian message (Macejak et. al. 1991 Nature). IRES elements can be linked to heterologous open reading frames. Multiple open reading frames can be transcribed together, each separated by an IRES, creating polycistronic messages. The IRES element enables each open reading frame to be accessible to ribosomes for efficient translation. Multiple genes can be efficiently expressed using a single promoter/enhancer to transcribe a single message (U.S. Pat. Nos. 5,925,565 and 5,935,819, each herein incorporated by reference). In certain embodiments, the Type I IFN and CD40-L are linked by IRES elements for efficient expression of both genes.

Further embodiments of the invention provide a composition comprising the APC, such as DC, or the oncolytic virus of the invention and a pharmaceutically acceptable carrier or an adjuvant.

As noted above, the invention provides that APCs, such as DCs, that express a combination of type I IFN and CD40-L induce a potent systemic T cell response when coupled with a cell death inducing treatment. Such effects can also be provided by administering oncolytic viruses expressing a combination of a type I IFN and CD40-L, for example, via one or more heterologous nucleic acid sequences encoding a combination of IFNβ and CD40-L.

Accordingly, certain embodiments of the invention provide a method for treating a malignancy, comprising administering to a subject in need of treatment an effective amount of APCs, such as DCs, or oncolytic viruses of the invention that express a combination of an exogenous type I IFN and an exogenous CD40-L, for example, via one or more heterologous nucleic acid sequences encoding a combination of IFNβ and CD40-L.

In preferred embodiments, the APCs, such as DCs, used in the methods of the invention are autologous APCs, i.e., APCs from a subject suffering from a malignancy are isolated and modified to express a combination of an exogenous type I IFN and an exogenous CD40-L, for example via one or more heterologous nucleic acid sequences encoding a combination of IFNβ and CD40-L, and administered to the subject. However, the APCs may be autologous, allogeneic, or xenogeneic.

APCs, such as DCs, or the oncolytic viruses of the invention comprising a combination of type I IFN and CD40-L can be administered alone or in combination with one or more additional anti-cancer agents. Such agents include a chemotherapeutic drug (e.g., melphalan), immunomodulator, adjuvant, anemia drug (e.g., erythropoietin), radiation therapy, stem cell transplant, chimeric antigen receptor (CAR)-expressing T-cells (CAR T-cells), or a combination of two or more of the foregoing. In certain embodiments, such therapy is administered before, during, or after administering the APCs, such as DCs, or the oncolytic viruses.

Optimal activity of APCs, such as DCs, of the invention may only be observed when there is an abundance of tumor antigens. A phenomenon observed in human cancer patients undergoing radiation treatment (IR) is the abscopal effect, where IR can induce regression of tumors outside of the field of radiation. The abscopal effect is based on T cell activation following IR-induced cell death leading to release of tumor antigens. The rarity of this effect may be because the necessary signals required for DC and T cell activation are not provided by IR alone. The abscopal effect is thought to be based on release of tumor antigens by IR leading to induction of an anti-tumor T cell immune response but the means to make the abscopal effect more commonplace in order to benefit a greater number of patients is not known.

The invention provides that radiation alone may not be sufficiently strong activator of innate immunity leading to DC activation and antigen presentation. Therefore, the invention provides that exogenous administration of stimulators of innate immunity will augment the anti-tumor T cell response leading to a greater abscopal effect.

One such stimulator of innate immunity is an APC, such as DC, comprising a combination of type I IFN and CD40-L, for example, a lentivirus transduced APC, such as DC, vaccine expressing high levels of a combination of IFNβ and CD40-L, which regulate APC, such as DC, activation. APCs, such as DCs, disclosed herein can be used for intra-tumor injection. The invention provides that combining IR and APCs comprising a combination of type I IFN and CD40-L, such as a combination of IFNβ and CD40-L, resulted in a potent anti-tumor abscopal effect through strong T cell activation. This treatment was especially effective when combined with checkpoint blockade therapy.

According to the invention, administering APCs, such as DCs, comprising a combination of type I IFN and CD40-L, such as, a combination of IFNβ and CD40-L, in irradiated tumors would enhance the abscopal effect.

Accordingly, in certain methods of treating a malignancy in the subject comprise administering an irradiation therapy to the subject followed by administering APCs, such as DCs, comprising a combination of an exogenous Type I IFN and an exogenous CD40-L, such as a combination of IFNβ and CD40-L, for example via one or more heterologous nucleic acid sequences encoding a combination of IFNβ and CD40-L. APCs, such as DCs, can be administered within about one day to about seven days, preferably, within about two days to about six days, more preferably within about three to five days, and even more preferably, within about four days. The APCs, such as DCs, can be administered multiple times over a period of days. In further embodiments, APCs, such as DCs, can be administered about 20 to 40 hours, preferably about 25 to 35 hours, even more preferably, about 30 hours, and most preferably, about 24 hours after administering irradiation.

Irradiation administered to a subject is preferably an ionizing irradiation, such as X-ray, gamma-ray, radon, or other forms of high-energy radiation.

In certain embodiments, the APCs, such as DCs, or the oncolytic viruses are administered by an intradermal injection, particularly, at an anatomical site that drains to the axillary and/or inguinal lymph node basins of the subject. In other embodiments, the APCs, such as DCs, or oncolytic viruses, are administered into the tumor (intra-tumorally) or into a lymph node, such as inguinal lymph node of the subject. In other embodiments, the APCs, such as DCs, or oncolytic viruses, are administered by an intravascular (e.g., intravenous) injection.

In some embodiments, in addition to administering an irradiation therapy and APCs, such as DCs, or administering the oncolytic viruses of the invention, the methods further comprise conducting hematopoietic cell transplantation (hematopoietic stem cells or progenitor cells, e.g., from bone marrow, peripheral blood, or cord blood) on the subject. The hematopoietic cell transplant can be autologous or allogeneic. APCs, such as DCs, or the oncolytic viruses of the invention can be administered before and/or after the hematopoietic cell transplantation.

In further embodiments, in addition to administering an irradiation therapy and APCs, such as DCs, or administering the oncolytic viruses of the invention, and optionally, conducting hematopoietic cell transplantation, the methods further comprise conducting stem cell mobilization (e.g., using G-CSF) on the subject and collecting the hematopoietic cells from the subject prior to autologous hematopoietic cell transplantation.

Typically, APCs, such as DCs, are collected from a subject, modified according to the invention and administered to the subject. APCs, such as DCs, can be cryopreserved prior to administering to a subject.

In certain embodiments, the methods comprise administering a chemotherapeutic agent (e.g., melphalan) before, during, or after administering APCs, such as DCs, or the oncolytic viruses of the invention.

In certain embodiments, after administering an irradiation therapy and APCs, such as DCs, or the oncolytic viruses of the invention, the methods further comprise administering a checkpoint inhibitor to the subject.

Certain checkpoint inhibitors have been used in cancer therapy. Checkpoints refer to inhibitory pathways in the immune system that are responsible for maintaining self-tolerance and modulating the degree of immune system response to minimize peripheral tissue damage. Tumor cells can activate immune system checkpoints to decrease the efficacy of immune response against tumor tissues. Administering checkpoint inhibitors release the inhibition on the immune system and allow immune system activity against the tumor cells. Exemplary checkpoint inhibitors include inhibitors, such as antibodies, against cytotoxic T-lymphocyte antigen 4 (CTLA4, also known as CD152), programmed cell death protein 1 (PD-1, also known as CD279) and programmed cell death 1 ligand 1 (PD-L1, also known as CD274). Exemplary anti-PD-1 antibodies are commercially available and include pembrolizumab, lambrolizumab, nivolumab, AMP-224, and pidilizumab. Exemplary anti-PD-L1 antibodies are also commercially available and include atezolizumab, MDX-1105, MEDI4736, MPDL3280A, BMS-936559, and MIH1. Exemplary anti-CTLA4 antibodies include ipilimumab and tremelimumab. Ipilimumab has received FDA approval for treatment of metastatic melanoma (Wada et al., 2013, J Transl Med 11:89). Additional examples of checkpoint protein targets include, but are not limited to, B7-H3, B7-H4, BTLA, HVEM, TIM3, GALS, LAG3, VISTA, KIR, 2B4 (belongs to the CD2 family of molecules and is expressed on all NK cells, and memory $CD8^+$ T cells), CD160 (also referred to as BY55), CGEN-15049, CHK 1 and CHK2 kinases, A2aR, and various B-7 family ligands. Non-limiting examples of antibodies include MEDI0680 (AMP-514), AUNP-12, avelumab (MSB0010718C), BMS935559 (MDX-1105), rHIgM12B7, BMS-986016, GSK2831781, IMP321, lirilumab (BMS-986015), IPH2101 (1-7F9), Indoximod (NLG 9189), NLG 919, INCB024360, PF-05082566, Urelumab (BMS-663513), and MEDI6469.

Non-limiting examples of checkpoint inhibitors that may be used are listed in Table 1 below.

TABLE 1

Examples of Checkpoint Inhibitors, Classes, and Target Molecules

| Name | Class of Agent | Target |
|---|---|---|
| Ipilumumab (a.k.a. MDX-010; MDX-101; BMS-734016; marketed as Yervoy) | IgG1 human mAb | Cytotoxic T-lymphocyte antigen 4 (CTLA-4) |
| Tremelimumab (a.k.a. ticilimumab; CP-675-206) | IgG2 human mAb | CTLA-4 |
| Nivolumab (a.k.a. ONO-4538; BMS-936558; MDX1106; marketed as Opdivo) | IgG4 human mAb | Programmed death-1 (PD-1) |

TABLE 1-continued

Examples of Checkpoint Inhibitors, Classes, and Target Molecules

| Name | Class of Agent | Target |
|---|---|---|
| Pembrolizumab (a.k.a., MK-3475; lambrolizumab; marketed as Keytruda) | IgG4 humanized mAb | PD-1 |
| Pidlizumab (a.k.a. CT-011) | IgG1 humanized mAb | PD-1 |
| MEDI0680 (a.k.a. AMP-514) | IgG4 humanized mAb | PD-1 |
| AMP-224 | Fc-PD-L2 fusion protein | PD-1 |
| AUNP-12 | Branched, 29-amino acid peptide | PD-1 |
| BMS-936559 | IgG4 human mAb | Programmed death ligand-1 (PD-L1) |
| Atezolizumab (a.k.a. MPDL3280A; RG7446) | IgG1 humanized mAb | PD-L1 |
| Durvalumab (a.k.a. MEDI4736) | IgG1 human mAb | PD-L1 |
| Avelumab (a.k.a. MSB0010718C) | IgG1 human mAb | PD-L1 |
| BMS935559 (a.k.a. MDX-1105) | IgG4 human mAb | PD-L1 |
| rHIgM12B7 | IgM human mAb | Programmed death ligand-2 (PD-L2) |
| BMS-986016 | mAB | Lymphocyte activation gene-3 (LAG-3; a.k.a. CD223) |
| GSK2831781 | Humanized afuscated mAb | LAG-3 |
| IMP321 | Soluble LAG-3 | LAG-3 |
| Lirilumab (a.k.a. BMS-986015) | IgG4 human mAb | Killer cell immunoglobulin-like receptor (KIR) |
| IPH2101 (a.k.a. 1-7F9) | Anti-inhibitor monoclonal Ab | KIR |
| Indoximod (a.k.a. NLG 9189; CAS #110117-83-4) | Small molecule (D isomer of 1-methyl-tryptophan) | (Indoleamine-2,3-dioxygenase 1 (IDO1) |
| NLG 919 (CAS # 1402836-58-1) | Small molecule | IDO1 |
| INCB024360 (CAS # 914471-09-3) | Small molecule | IDO1 |
| PF-05082566 | IgG2 human mAB | 4-1BB (a.k.a. CD137) |
| Urelumab (a.k.a. BMS-663513) | IgG4 humanized mAb | 4-1BB |
| MEDI6469 | IgG1 mouse anti-human Ab | OX40 (a.k.a. CD134) |

In one embodiment, a combination of two or more checkpoint inhibitors is administered to the subject. In one embodiment, the combination of checkpoint inhibitors is selected from among those in Table 1. The two or more checkpoint inhibitors can be administered simultaneously or consecutively with respect to one another. In a further embodiment, the combination of two or more checkpoint inhibitors target two different checkpoint proteins, such as PD-1 (e.g., nivolumab or other PD-1 inhibitor) and CTLA-4 (e.g., ipilumumab or other CTLA-4 inhibitor), are administered to the subject simultaneously or consecutively with respect to one another. In one embodiment, the combination of two or more checkpoint inhibitors target two or more different checkpoint proteins from among: CTLA-4, PD-L1, PD-L2, PD1, B7-H3, B7-H4, BTLA, HVEM, TIM3, GALS, LAG3, VISTA, KIR, 2B4, CD160, CGEN-15049, CHK 1 kinase, CHK2 kinase, A2aR, and B-7 family ligands. In one embodiment, the combination of two or more checkpoint inhibitors targeting two or more different checkpoint proteins is selected from among those in Table 1.

The dose level, frequency of dosing, duration of dosing and other aspects of administration of the checkpoint inhibitor may be optimized in accordance with the patient's clinical presentation, duration or course of the disease, comorbidities, and other aspects of clinical care. The invention is not so limiting with regard to the particular aspects of the checkpoint inhibitor component of the methods embodied herein. Additional checkpoint inhibitors are well known to a skilled artisan and such embodiments are within the purview of the invention.

Examples of cancers that can be treated according to the materials and methods disclosed herein include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is melanoma, MDS, ovarian cancer, breast cancer, or multiple myeloma.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may be treated with the compositions and methods of the invention are listed in Table 2.

TABLE 2

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult (Primary) |
| Acute Myeloid Leukemia, Childhood | Hepatocellular (Liver) Cancer, Childhood (Primary) |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, Childhood |
| Astrocytoma, Childhood Cerebellar | Intraocular Melanoma |
| Astrocytoma, Childhood Cerebral | Islet Cell Carcinoma (Endocrine Pancreas) |
| Basal Cell Carcinoma | Kaposi's Sarcoma |
| Bile Duct Cancer, Extrahepatic | Kidney (Renal Cell) Cancer |
| Bladder Cancer | Kidney Cancer, Childhood |
| Bladder Cancer, Childhood | Laryngeal Cancer |
| Bone Cancer, Osteosarcoma/Malignant Fibrous Histiocytoma | Laryngeal Cancer, Childhood |
| Brain Stem Glioma, Childhood | Leukemia, Acute Lymphoblastic, Adult |
| Brain Tumor, Adult | Leukemia, Acute Lymphoblastic, Childhood |
| Brain Tumor, Brain Stem Glioma, Childhood | Leukemia, Acute Myeloid, Adult |
| Brain Tumor, Cerebellar Astrocytoma, Childhood | Leukemia, Acute Myeloid, Childhood |
| Brain Tumor, Cerebral Astrocytoma/Malignant Glioma, Childhood | Leukemia, Chronic Lymphocytic |
| Brain Tumor, Ependymoma, Childhood | Leukemia, Chronic Myelogenous |
| Brain Tumor, Medulloblastoma, Childhood | Leukemia, Hairy Cell |
| Brain Tumor, Supratentorial Primitive Neuroectodermal Tumors, Childhood | Lip and Oral Cavity Cancer |
| Brain Tumor, Visual Pathway and Hypothalamic Glioma, Childhood | Liver Cancer, Adult (Primary) |
| Brain Tumor, Childhood | Liver Cancer, Childhood (Primary) |
| Breast Cancer | Lung Cancer, Non-Small Cell |
| Breast Cancer, Childhood | Lung Cancer, Small Cell |
| Breast Cancer, Male | Lymphoma, AIDS-Related |
| Bronchial Adenomas/Carcinoids, Childhood | Lymphoma, Burkitt's |
| Burkitt's Lymphoma | Lymphoma, Cutaneous T-Cell, see Mycosis Fungoides and Sézary Syndrome |
| Carcinoid Tumor, Childhood | Lymphoma, Hodgkin's, Adult |
| Carcinoid Tumor, Gastrointestinal | Lymphoma, Hodgkin's, Childhood |
| Carcinoma of Unknown Primary | Lymphoma, Hodgkin's During Pregnancy |
| Central Nervous System Lymphoma, Primary | Lymphoma, Non-Hodgkin's, Adult |
| Cerebellar Astrocytoma, Childhood | Lymphoma, Non-Hodgkin's, Childhood |
| Cerebral Astrocytoma/Malignant Glioma, Childhood | Lymphoma, Non-Hodgkin's During Pregnancy |
| Cervical Cancer | Lymphoma, Primary Central Nervous System |
| Childhood Cancers | Macroglobulinemia, Waldenström's |
| Chronic Lymphocytic Leukemia | Malignant Fibrous Histiocytoma of Bone/Osteosarcoma |
| Chronic Myelogenous Leukemia | Medulloblastoma, Childhood |
| Chronic Myeloproliferative Disorders | Melanoma |
| Colon Cancer | Melanoma, Intraocular (Eye) |
| Colorectal Cancer, Childhood | Merkel Cell Carcinoma |
| Cutaneous T-Cell Lymphoma, see Mycosis Fungoides and Sézary Syndrome | Mesothelioma, Adult Malignant |
| | Mesothelioma, Childhood |
| | Metastatic Squamous Neck Cancer with Occult Primary |
| | Multiple Endocrine Neoplasia Syndrome, |

TABLE 2-continued

| Examples of Cancer Types | |
|---|---|
| Endometrial Cancer | Childhood |
| Ependymoma, Childhood | Multiple Myeloma/Plasma Cell Neoplasm |
| Esophageal Cancer | Mycosis Fungoides |
| Esophageal Cancer, Childhood | Myelodysplastic Syndromes |
| Ewing's Family of Tumors | Myelodysplastic/Myeloproliferative Diseases |
| Extracranial Germ Cell Tumor, Childhood | Myelogenous Leukemia, Chronic |
| Extragonadal Germ Cell Tumor | Myeloid Leukemia, Adult Acute |
| Extrahepatic Bile Duct Cancer | Myeloid Leukemia, Childhood Acute |
| Eye Cancer, Intraocular Melanoma | Myeloma, Multiple |
| Eye Cancer, Retinoblastoma | Myeloproliferative Disorders, Chronic |
| Gallbladder Cancer | Nasal Cavity and Paranasal Sinus Cancer |
| Gastric (Stomach) Cancer | Nasopharyngeal Cancer |
| Gastric (Stomach) Cancer, Childhood | Nasopharyngeal Cancer, Childhood |
| Gastrointestinal Carcinoid Tumor | Neuroblastoma |
| Germ Cell Tumor, Extracranial, | Non-Hodgkin's Lymphoma, Adult |
| Childhood | Non-Hodgkin's Lymphoma, Childhood |
| Germ Cell Tumor, Extragonadal | Non-Hodgkin's Lymphoma During Pregnancy |
| Germ Cell Tumor, Ovarian | Non-Small Cell Lung Cancer |
| Gestational Trophoblastic Tumor | Oral Cancer, Childhood |
| Glioma, Adult | Oral Cavity Cancer, Lip and |
| Glioma, Childhood Brain Stem | Oropharyngeal Cancer |
| Glioma, Childhood Cerebral | Osteosarcoma/Malignant Fibrous |
| Astrocytoma | Histiocytoma of Bone |
| Glioma, Childhood Visual Pathway | Ovarian Cancer, Childhood |
| and Hypothalamic | Ovarian Epithelial Cancer |
| Skin Cancer (Melanoma) | Ovarian Germ Cell Tumor |
| Skin Carcinoma, Merkel Cell | Ovarian Low Malignant Potential Tumor |
| Small Cell Lung Cancer | Pancreatic Cancer |
| Small Intestine Cancer | Pancreatic Cancer, Childhood |
| Soft Tissue Sarcoma, Adult | Pancreatic Cancer, Islet Cell |
| Soft Tissue Sarcoma, Childhood | Paranasal Sinus and Nasal Cavity Cancer |
| Squamous Cell Carcinoma, see Skin | Parathyroid Cancer |
| Cancer (non-Melanoma) | Penile Cancer |
| Squamous Neck Cancer with Occult | Pheochromocytoma |
| Primary, Metastatic | Pineoblastoma and Supratentorial Primitive |
| Stomach (Gastric) Cancer | Neuroectodermal Tumors, Childhood |
| Stomach (Gastric) Cancer, Childhood | Pituitary Tumor |
| Supratentorial Primitive | Plasma Cell Neoplasm/Multiple Myeloma |
| Neuroectodermal Tumors, Childhood | Pleuropulmonary Blastoma |
| T-Cell Lymphoma, Cutaneous, see | Pregnancy and Breast Cancer |
| Mycosis Fungoides and Sézary | Pregnancy and Hodgkin's Lymphoma |
| Syndrome | Pregnancy and Non-Hodgkin's Lymphoma |
| Testicular Cancer | Primary Central Nervous System Lymphoma |
| Thymoma, Childhood | Prostate Cancer |
| Thymoma and Thymic Carcinoma | Rectal Cancer |
| Thyroid | Renal Cell (Kidney) Cancer |
| Cancer | Renal Cell (Kidney) Cancer, Childhood |
| Thyroid Cancer, Childhood | Renal Pelvis and Ureter, Transitional Cell |
| Transitional Cell Cancer of the Renal | Cancer |
| Pelvis and Ureter | Retinoblastoma |
| Trophoblastic Tumor, Gestational | Rhabdomyosarcoma, Childhood |
| Unknown Primary Site, Carcinoma of, | Salivary Gland Cancer |
| Adult | Salivary Gland Cancer, Childhood |
| Unknown Primary Site, Cancer of, | Sarcoma, Ewing's Family of Tumors |
| Childhood | Sarcoma, Kaposi's |
| Unusual Cancers of Childhood | Sarcoma, Soft Tissue, Adult |
| Ureter and Renal Pelvis, Transitional | Sarcoma, Soft Tissue, Childhood |
| Cell Cancer | Sarcoma, Uterine |
| Urethral Cancer | Sezary Syndrome |
| Uterine Cancer, Endometrial | Skin Cancer (non-Melanoma) |
| Uterine Sarcoma | Skin Cancer, Childhood |
| Vaginal Cancer | |
| Visual Pathway and Hypothalamic | |
| Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. Some tumors are unresectable (cannot be surgically removed due to, for example the number of metastatic foci or because it is in a surgical danger zone). The treatment and prognostic methods of the invention can be utilized for early, middle, or late stage disease, and acute or chronic disease.

Compositions and Treatments

Various methods may be used to deliver a combination of a type I IFN and CD40-L, such as a combination of IFNβ and CD40-L, or deliver a nucleic acid sequence encoding a combination of a type I IFN and CD40-L, such as a combination of IFNβ and CD40-L, to produce an APC, particular DC, or an oncolytic virus of the invention.

Examples of methods that may be utilized to deliver the combination of a type I IFN and CD40-L polypeptide, or one or more nucleic acid molecules encoding a combination of a type I IFN and CD40-L to produce the APCs, such as DCs, of the invention include, but are not limited to, viral vectors, such as retrovirus, adenovirus, adeno-associated virus, lentivirus, vesicular stomatitis virus, or herpes simplex virus; nanoparticles; naked or packed protein; gene editing systems such as TALEN (Transcription Activator-Like Effector Nucleases) or CRISPR (Clustered Regulatory Interspaced Short Palindromic Repeats)/Cas9 systems (see, for example, Nemudryi A A et al., *Acta Naturae,* 2014 July-September, 6(3):19-40, which is incorporated herein by reference); DNA (naked or packaged); mRNA (naked or packaged); electroporation; sonoporation; gene gun, gold or other metal particles; magnetofication; hydrodynamic delivery; DNA plasmid; siiRNA, oligonucleotides, lipoplexes; lipoproteins, homing nucleases; polymersomes; polyplexes; transposon (e.g., sleeping beauty transposon, see for example, Ivics Z et al., *Hum Gene Ther* 2011, 22(9):1043-1051, which is incorporated herein by reference in its entirety); dendrimer; macromolecule; inorganic nanoparticle; quantum dot, cell penetrating peptide (also known as a peptide transduction domain) such as HIV TAT protein, Antennapedia transduction domain, transportan, or polyarginine (see, for example, Copolovici D M et al., *ACS Nano,* 2014, 8(3):1972-1994; Wagstaff K M et al., *Curr Meth Chem,* 2006, 13(12):1371-87, and Trabulo S et al., *Pharmaceuticals,* 2010, 3:961-993, which are incorporated herein by reference in their entirety); virosome; hybridizing virus; bacteriophage; or gene targeting.

Methods for making APC, such as DC, vaccines with other tumor antigens and their use for cancer immunotherapy are known and may be used with the combination of type I IFN and CD40-L described herein (see, for example, Palucka K et al., *Nature Reviews Cancer,* 2012, 12:265-277, which is incorporated herein by reference in its entirety).

Viral or non-viral gene delivery methods may be used to transduce cells such as APCs, such as DCs, with one or more nucleic acid sequences encoding a combination of a type I IFN and CD40-L.

Examples of viral vectors that may be used to deliver nucleic acid sequences include but are not limited to adenovirus (AV), adeno-associated virus (AAV), poxvirus, lentivrus, alphavirus, herpesvirus, retrovirus, and vaccinia virus. When used in an APC, such as DC, the virus is typically replication deficient.

Non-viral methods for gene delivery include, but are not limited to, naked DNA injection, inorganic particles, synthetic or natural biodegradable particles, as well as physical methods such as needle injection, ballistic DNA injection, electroporation, sonoporation, photoporation, magnetofectoin, and hydroporation. Examples of inorganic particles include calcium phosphate, silica, gold, and magnetic particles. Examples of synthetic or natural biodegradable particles include polymeric-based non-viral vectors such as poly(lactic-co-glycolic acid (PLGA), poly lactic acid (PLA), poly(ethylene imine4) (PEI), chitosan, dendrimers, and polymethacrylates; cationic lipid-based non-viral vectors such as cationic liposomes, cationic emulsions, and solid lipid nanoparticles; and peptide-based non-viral vectors such as poly-L-lysine.

Optionally, APCs, such as DCs, or oncolytic viruses of the invention can be co-administered, simultaneously or consecutively, with one or more other agents to a subject. Anti-cancer agents that may be administered include but are not limited to those listed in Tables 1 and 3.

Co-administration can be carried out simultaneously (in the same or separate formulations) or consecutively with the additional agent administered before and/or after one or more compounds disclosed herein.

Thus, APCs, such as DCs, or oncolytic viruses of the invention, whether administered separately, or as a pharmaceutical composition, can include various other components. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, antiangiogenics, anti-pyretics, time-release binders, anesthetics, steroids, and corticosteroids. Such components can provide additional therapeutic benefit, act to affect the therapeutic action of the APCs, such as DCs, or act towards preventing any potential side effects which may be posed as a result of administration of the compounds.

Additional agents that can be co-administered to target cells in vitro or in vivo, such as in a subject, in the same or as a separate formulation, include those that modify a given biological response, such as immunomodulators. The additional agents may be, for example, small molecules, polypeptides (proteins, peptides, or antibodies or antibody fragments), or nucleic acids (encoding polypeptides or inhibitory nucleic acids such as antisense oligonucleotides or interfering RNA). For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more anti-cancer agents, such as cytotoxic agents, chemotherapeutic agents, anti-signaling agents, and anti-angiogenic agents.

In some embodiments, the compositions of the invention include at least one additional anti-cancer agent (e.g., a chemotherapeutic agent). In some embodiments of the methods of the invention, at least one additional anti-cancer agent is administered with the compositions of the invention. In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor.

In some embodiments, the compositions can include, and the methods can include administration of, one or more proteasome inhibitors (e.g., bortezomib), inhibitors of autophagy (e.g., chloroquine), alkylating agents (e.g., melphalan, cyclophosphamide), MEK inhibitors (e.g., PD98509), FAK/PYK2 inhibitors (e.g., PF562271), or EGFR inhibitors (e.g., erlotinib, gefitinib, cetuximab, panitumumab, zalutumumab, nimotuzumab, matuzumab), or a combination of two or more of the foregoing.

Thus, immunotherapeutics, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The immunotherapeutic agent can be conjugated to a therapeutic agent or other agent, as well.

As used herein, the term "immunotherapy" refers to the treatment of disease via the stimulation, induction, subversion, mimicry, enhancement, augmentation or any other modulation of a subject's immune system to elicit or amplify adaptive or innate immunity (actively or passively) against cancerous or otherwise harmful proteins, cells or tissues. Immunotherapies (i.e., immunotherapeutic agents) include cancer vaccines, immunomodulators, monoclonal antibodies (e.g., humanized monoclonal antibodies), immunostimulants, dendritic cells, and viral therapies, whether designed to treat existing cancers or prevent the development of cancers or for use in the adjuvant setting to reduce likelihood of recurrence of cancer. Examples of cancer vaccines include GVAX, Stimuvax, DCVax and other vaccines designed to elicit immune responses to tumor and other antigens including MUC1, NY-ESO-1, MAGE, p53 and others. Examples of immunomodulators include 1MT, Ipilimumab, Tremelimumab and/or any drug designed to de-repress or otherwise modulate cytotoxic or other T cell activity against tumor or other antigens, including, but not restricted to, treatments that modulate T-Reg cell control pathways via CTLA-4, CD80, CD86, MHC, B7-DC, B7-H1, B7-H2, B7-H3, B7-H4, CD28, other TCRs, PD-1, PDL-1, ICOS and their ligands, whether via blockade, agonist or antagonist. Examples of immunostimulants include corticosteroids and any other anti- or pro-inflammatory agent, steroidal or non-steroidal, including, but not restricted to, GM-CSF, interleukins (e.g., IL-2, IL-7, IL-12), cytokines such as the interferons, and others. Examples of dendritic cell (DC) therapies include modified dendritic cells and any other antigen presenting cell, autologous or xeno, whether modified by multiple antigens, whole cancer cells, single antigens, by mRNA, phage display or any other modification, including but not restricted to ex vivo-generated, antigen-loaded dendritic cells (DCs) to induce antigen-specific T-cell immunity, ex vivo gene-loaded DCs to induce humoral immunity, ex vivo-generated antigen-loaded DCs induce tumour-specific immunity, ex vivo-generated immature DCs to induce tolerance, including but not limited to Provenge and others. Examples of viral therapies include oncolytic viruses or virus-derived genetic or other material designed to elicit anti-tumor immunity and inhibitors of infectious viruses associated with tumor development, such as drugs in the Prophage series. Examples of monoclonal antibodies include Alemtuzumab, Bevacizumab, Cetuximab, Gemtuzumab ozogamicin, Rituximab, Trastuzumab, Radioimmunotherapy, Ibritumomab tiuxetan, Tositumomab/iodine tositumomab regimen. An immunotherapy may be a monotherapy or used in combination with one or more other therapies (one or more other immunotherapies or non-immunotherapies).

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel and docetaxel, chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene, and anti-androgens such as flutamide, nilutamide, bicalutamide, leuprolide, and goserelin. Examples of anti-cancer agents, including chemotherapeutic agents, that may be used in conjunction with the compounds of the invention are listed in Table 3. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin, doxorubicin, epirubicin, and idarubicin.

TABLE 3

| Examples of Anti-Cancer Agents | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |

TABLE 3-continued

| Examples of Anti-Cancer Agents | |
|---|---|
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with |
| BCG | Carmustine implant |
| BCNU | Purinethol |
| Bevacizumab | Raloxifene |
| Bexarotene | Rheumatrex |
| Bicalutamide | Rituxan |
| BiCNU | Rituximab |
| Blenoxane | Roveron-A (interferon alfa-2a) |
| Bleomycin | Rubex |
| Bortezomib | Rubidomycin hydrochloride |
| Busulfan | Sandostatin |
| Busulfex | Sandostatin LAR |
| C225 | Sargramostim |
| Calcium Leucovorin | Solu-Cortef |
| Campath | Solu-Medrol |
| Camptosar | STI-571 |
| Camptothecin-11 | Streptozocin |
| Capecitabine | Tamoxifen |
| Carac | Targretin |
| Carboplatin | Taxol |
| Carmustine | Taxotere |
| Carmustine wafer | Temodar |
| Casodex | Temozolomide |
| CCNU | Teniposide |
| CDDP | TESPA |
| CeeNU | Thalidomide |
| Cerubidine | Thalomid |
| cetuximab | TheraCys |
| Chlorambucil | Thioguanine |
| Cisplatin | Thioguanine Tabloid |
| Citrovorum Factor | Thiophosphoamide |
| Cladribine | Thioplex |
| Cortisone | Thiotepa |
| Cosmegen | TICE |
| CPT-11 | Toposar |
| Cyclophosphamide | Topotecan |
| Cytadren | Toremifene |
| Cytarabine | Trastuzumab |
| Cytarabine liposomal | Tretinoin |
| Cytosar-U | Trexall |
| Cytoxan | Trisenox |
| Dacarbazine | TSPA |
| Dactinomycin | VCR |
| Darbepoetin alfa | Velban |
| Daunomycin | Velcade |
| Daunorubicin | VePesid |
| Daunorubicin | Vesanoid |
| hydrochloride | Viadur |
| Daunorubicin liposomal | Vinblastine |
| DaunoXome | Vinblastine Sulfate |
| Decadron | Vincasar Pfs |
| Delta-Cortef | Vincristine |
| Deltasone | Vinorelbine |
| Denileukin diftitox | Vinorelbine tartrate |
| DepoCyt | VLB |
| Dexamethasone | VP-16 |
| Dexamethasone acetate | Vumon |
| dexamethasone sodium | Xeloda |
| phosphate | Zanosar |
| Dexasone | Zevalin |
| Dexrazoxane | Zinecard |
| DHAD | Zoladex |
| DIC | Zoledronic acid |

TABLE 3-continued

| Examples of Anti-Cancer Agents | |
|---|---|
| Diodex | Zometa |
| Docetaxel | Gliadel wafer |
| Doxil | Glivec |
| Doxorubicin | GM-CSF |
| Doxorubicin liposomal | Goserelin |
| Droxia | granulocyte - colony stimulating factor |
| DTIC | Granulocyte macrophage colony |
| DTIC-Dome | stimulating factor |
| Duralone | Halotestin |
| Efudex | Herceptin |
| Eligard | Hexadrol |
| Ellence | Hexalen |
| Eloxatin | Hexamethylmelamine |
| Elspar | HMM |
| Emcyt | Hycamtin |
| Epirubicin | Hydrea |
| Epoetin alfa | Hydrocort Acetate |
| Erbitux | Hydrocortisone |
| Erwinia L-asparaginase | Hydrocortisone sodium phosphate |
| Estramustine | Hydrocortisone sodium succinate |
| Ethyol | Hydrocortone phosphate |
| Etopophos | Hydroxyurea |
| Etoposide | Ibritumomab |
| Etoposide phosphate | Ibritumomab Tiuxetan |
| Eulexin | Idamycin |
| Evista | Idarubicin |
| Exemestane | Ifex |
| Fareston | IFN-alpha |
| Faslodex | Ifosfamide |
| Femara | IL-2 |
| Filgrastim | IL-11 |
| Floxuridine | Imatinib mesylate |
| Fludara | Imidazole Carboxamide |
| Fludarabine | Interferon alfa |
| Fluoroplex | Interferon Alfa-2b (PEG conjugate) |
| Fluorouracil | Interleukin-2 |
| Fluorouracil (cream) | Interleukin-11 |
| Fluoxymesterone | Intron A (interferon alfa-2b) |
| Flutamide | Leucovorin |
| Folinic Acid | Leukeran |
| FUDR | Leukine |
| Fulvestrant | Leuprolide |
| G-CSF | Leurocristine |
| Gefitinib | Leustatin |
| Gemcitabine | Liposomal Ara-C |
| Gemtuzumab ozogamicin | Liquid Pred |
| Gemzar | Lomustine |
| Gleevec | L-PAM |
| Lupron | L-Sarcolysin |
| Lupron Depot | Meticorten |
| Matulane | Mitomycin |
| Maxidex | Mitomycin-C |
| Mechlorethamine | Mitoxantrone |
| Mechlorethamine | M-Prednisol |
| Hydrochlorine | MTC |
| Medralone | MTX |
| Medrol | Mustargen |
| Megace | Mustine |
| Megestrol | Mutamycin |
| Megestrol Acetate | Myleran |
| Melphalan | Iressa |
| Mercaptopurine | Irinotecan |
| Mesna | Isotretinoin |
| Mesnex | Kidrolase |
| Methotrexate | Lanacort |
| Methotrexate Sodium | L-asparaginase |
| Methylprednisolone | LCR |

While APCs, such as DCs, or oncolytic viruses of the invention can be administered to subjects as isolated agents, it is preferred to administer these cells or viruses as part of a pharmaceutical composition. The subject invention thus further provides compositions comprising the described APCs, such as DCs, or oncolytic viruses in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compositions administered in accordance with the methods of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, $19^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compositions of the invention, APCs, such as DCs, or oncolytic viruses, and others agents used in the methods of the invention may be locally administered at one or more anatomical sites, such as sites of unwanted cell growth (such as a tumor site, e.g., injected or topically applied to the tumor), optionally in combination with a pharmaceutically acceptable carrier such as an inert diluent. Compositions of the invention and other agents used in the methods of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the agents may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compositions and agents may be incorporated into sustained-release preparations and devices.

The active agents (e.g., APCs, such as DCs, or oncolytic viruses) of the invention can be administered into the tumor (intra-tumorally) or into a lymph node, such as inguinal lymph node of the subject. The active agents of the invention may also be administered intradermally, intravenously, or intraperitoneally by infusion or injection. In some embodiments, the APCs, such as DCs, are administered by intradermal injection, such as at an anatomical site that drains to the axillary and/or inguinal lymph node basins of the subject. Solutions of the active agents can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the APCs, such as DCs, or oncolytic viruses of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the APCs, such as DCs, or oncolytic viruses and other agents in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compositions and agents may be applied in pure-form, i.e., when they are liquids. However, it will generally be desirable to administer them topically to the skin as compositions, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Additives such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising the APCs, such as DCs, or oncolytic viruses, optionally, in combination with a pharmaceutically acceptable carrier. Pharmaceutical compositions adapted for oral, topical or parenteral administration, comprising an amount of APCs, such as DCs, or oncolytic viruses constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition. Advantageously, in some embodiments, administration of the compounds of the invention does not induce weight loss or overt signs of toxicity in the subject.

Depending upon the disorder or disease condition to be treated (e.g., a malignancy such as myeloma), a suitable dose(s) may be that amount that will reduce proliferation or growth of the target cell(s), or induce cell death. In the context of cancer, a suitable dose(s) results in a concentration of the active agent in cancer tissue, such as a malignant tumor, which is known to achieve the desired response. The preferred dosage is the amount which results in maximum inhibition of cancer cell growth, without unmanageable side effects. Administration of the APCs, such as DCs, or oncolytic viruses and other agents can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the agents of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Preparation of APCs, such as, DCs

APCs are important in eliciting an effective immune response. APCs not only present antigens to T cells with antigen-specific receptors, but also provide the signals necessary for T cell activation. Such signals remain incompletely defined, but are known to involve a variety of cell surface molecules as well as cytokines or growth factors. The factors necessary for the activation of naive or unprimed T cells may be different from those required for the re-activation of previously primed memory T cells. Although monocytes and B cells have been shown to be competent APC, their antigen presenting capacities appear to be limited to the re-activation of previously sensitized T cells. Hence, they are not capable of directly activating functionally naive or unprimed T cell populations. On the other hand, DCs are capable of both activating naive and previously primed T cells.

DCs have a distinctive morphology and a widespread tissue distribution, including blood. The cell surface of dendritic cells is unusual, with characteristic veil-like projections. Mature dendritic cells are generally identified as CD3−, CD11c+, CD19−, CD83+, CD86+ and HLA-DR+.

DCs process and present antigens and stimulate responses from naive and unprimed T cells and memory T cells. In particular, DCs have a high capacity for sensitizing MHC-restricted T cells and are very effective at presenting antigens to T cells, both self-antigens during T cell development and tolerance, and foreign antigens during an immune response. In addition to their role in antigen presentation, DCs also directly communicate with non-lymph tissue and survey non-lymph tissue for an injury signal (e.g., ischemia, infection, or inflammation) or tumor growth. Once signaled, DCs initiate an immune response by releasing cytokines that stimulate activity of lymphocytes and monocytes.

Due to their effectiveness at antigen presentation, DCs may be used as an immunostimulatory agent, both in vivo and ex vivo. The use of isolated DCs as immunostimulatory agents has been limited, however, due to the low frequency of DCs in peripheral blood and the low purity of DCs isolated by prior methods. In particular, the frequency of DCs in human peripheral blood has been estimated at about 0.1% of the white cells. Similarly, there is limited accessibility of DCs from other tissues, such as lymphoid organs. The low frequency of DCs has increased interest in isolating cell population enriched in DC precursors and culturing these precursors ex vivo or in vitro to obtain enriched populations of immature or mature DCs. Because the characteristics of DC precursors remain incompletely defined, methods typically used for isolating DC precursors do not result in purified fractions of the desired precursors, but instead generally produce mixed populations of leukocytes enriched in DC precursors. Several cell types have been identified as having the potential to function as DC precursors. Blood-derived $CD14^+$ monocytes, especially those that express on their surface the receptor for the growth factor granulocyte-monocyte colony stimulating factor (GM-CSF) are known DC precursors. Other blood-derived DC precursors can be isolated by first removing monocytes and other "non-dendritic cell precursors." (See, e.g., U.S. Pat. Nos. 5,994,126 and 5,851,756.). Other known DC precursors include bone marrow-derived cells that express the CD34 cell surface marker.

Cell populations enriched in DC precursors have been obtained by various methods and may be utilized with the invention, such as, for example, density gradient separation, fluorescence activated cell sorting, immunological cell separation techniques, e.g., panning, complement lysis, rosetting, magnetic cell separation techniques, nylon wool separation, and combinations of such methods. (See, e.g., O'Doherty et al., *J. Exp. Med.* 178:1067-76 (1993); Young and Steinman, *J. Exp. Med.* 171:1315-32 (1990); Freudenthal and Steinman, *Proc. Natl. Acad. Sci. USA* 87:7698-702 (1990); Macatonia et al., *Immunol.* 67:285-89 (1989); Markowicz and Engleman, *J. Clin. Invest.* 85:955-61 (1990) all incorporated herein by reference in their entirety). Methods for immunoselecting DCs include, for example, using antibodies to cell surface markers associated with dendritic cell precursors, such as anti-CD34 and/or anti-CD14 antibodies coupled to a substrate. (See, e.g., Bernhard et al., *Cancer Res.* 55:1099-104 (1995); Caux et. al., *Nature* 360:258-61 (1992)).

In one typical example method, leukocytes are isolated by a leukapheresis procedure. Additional methods are typically used for further purification to enrich for cell fractions thought to contain DCs and/or DC precursors. Similarly, methods such as differential centrifugation (e.g., isolation of a buffy coat), panning with monoclonal antibodies specific for certain cell surface proteins (e.g., positive and negative selection), and filtration also produce a crude mixture of leukocytes containing DC precursors.

Another reported method for isolating proliferating DC precursors is to use a commercially treated plastic substrate (e.g., beads or magnetic beads) to selectively remove adherent monocytes and other "non-dendritic cell precursors." (See, e.g., U.S. Pat. Nos. 5,994,126 and 5,851,756). The adherent monocytes and non-DC precursors are discarded while the non-adherent cells are retained for ex vivo culture and maturation. In another method, apheresis cells were cultured in plastic culture bags to which plastic, i.e., polystyrene or styrene, microcarrier beads were added to increase the surface area of the bag. The cells were cultured for a sufficient period of time for cells to adhere to the beads and the non-adherent cells were washed from the bag. (Maffei, et al., Transfusion 40:1419-1420 (2000); WO 02/44338, incorporated herein by reference).

Subsequent to essentially all of the reported methods for the preparation of a cell population enriched for DC precursors, the cell populations are typically cultured ex vivo or in vitro for differentiation of the DC precursors or maintenance, and/or expansion of the DCs. Briefly, ex vivo differentiation of monocytic DC precursors has involved culturing the mixed cell populations enriched for DC precursors in the presence of combinations of cellular growth factors, such as cytokines. For example, monocytic DC precursors require granulocyte/monocyte colony-stimulating factor (GM-CSF) in combination with at least one other cytokine selected from, for example, either Interleukin 4 (IL-4), Interleukin 15 (IL-15), Interleukin 13 (IL-13), interferon α (IFN-α), and the like, to differentiate the cells into an optimal state for antigen uptake, processing, and/or presentation. The numbers of DCs from non-monocytic DC precursors, such as those obtained by removal of monocytes and other non-DC precursor cells (adsorption to a plastic surface) or selection for $CD34^+$ cells, have also been expanded by culture in the presence of certain cytokines. Either GM-CSF alone or a combination of GM-CSF and IL-4 has been used in methods to produce DC populations from such proliferating DC precursors for therapeutic use.

The effectiveness of such ex vivo differentiation, maintenance and/or expansion has been limited, however, by the quality of the starting population enriched in DCs and DC precursors. Under some culture conditions, populations of DCs and DC precursors that are heavily contaminated with neutrophils, macrophages and lymphocytes, or combinations thereof, can be overtaken by the latter cells, resulting in a poor yield of DCs. Culture of DCs containing large numbers of neutrophils, macrophages and lymphocytes, or combinations thereof, are less suitable for use as immunostimulatory preparations.

APCs, such as DCs, can be administered to a subject to stimulate an immune response by bolus injection, by continuous infusion, sustained release from implants, or other suitable techniques known in the art. The APCs, such as DCs, also can be co-administered with physiologically acceptable carriers, excipients, buffers and/or diluents. Further, APCs, such as DCs, can be used to activate T cells, e.g., cytotoxic T cells, ex vivo using methods well known to the skilled artisan. These compositions can be used by themselves or as an adjuvant to other therapies, such as, for example, surgical resection, chemotherapy, radiation therapy, chimeric antigen receptor (CAR)-expressing T-cells (CAR T-cells), and combinations thereof, as well as other therapeutic modalities appropriate for the condition being treated.

Definitions

The terms "comprising", "consisting of" and "consisting essentially of" are defined according to their standard meaning. The terms may be substituted for one another throughout the instant application to attach the specific meaning associated with each term.

The terms "isolated" or "biologically pure" refer to material that is substantially or essentially free from components which normally accompany the material as it is found in its native state. Thus, compounds in accordance with the invention preferably do not contain materials normally associated with the peptides in their in situ environment.

As used in this specification, the singular forms "a", "an", and "the" include plural reference unless the context clearly dictates otherwise. Thus, for example, a reference to "a compound" includes more than one such compound. A reference to "a cell" includes more than one such cell, and so forth.

As used herein, the term "oncolytic virus" refers to a class of cancer therapeutic virus having one or both of the following mechanisms of action: 1) tumor cell killing through selective viral replication in tumor cells resulting in direct tumor lysis, and 2) induction of systemic anti-tumor immunity by releasing antigens from destroyed tumor cells.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

In an APC, such as a DC, containing a combination of an exogenous Type I IFN and an exogenous CD40-L, such as a combination of IFNβ and CD40-L, the type I IFN and CD40-L is expressed via one or more heterologous nucleic acid sequences containing heterologous genes encoding the type I IFN and CD40-L, i.e., genes other than naturally occurring genes within the APC, such as DC. The heterologous genes encoding the type I IFN and CD40-L may have the same sequence as the naturally occurring corresponding genes present in the APC, such as DC. The heterologous genes may have different sequences compared to the corresponding naturally occurring genes present in the APC, such as DC. The heterologous genes may encode for the same or different type I IFN and/or same or different CD40-L than encoded by the corresponding naturally occurring genes in the APC, such as DC.

The term "cleavage site" of a CD40-L refers to a sequence of amino acids that is recognized by proteases, such as matrix metalloproteases. Proteases cleave CD40-L from the surface of the cell on which the CD40-L is expressed. The cleavage site of CD40-L is typically found at or around the boundaries of domains III and IV of CD40-L. One such cleavage site is located in the region approximately between amino acids 108 and 116 of SEQ ID NO: 6.

A CD40-L that is less susceptible to cleavage refers to a higher resistance of a chimeric CD40-L to proteolytic cleavage compared to that of native human CD40-L. Susceptibility of a chimeric CD40-L to cleavage is typically measured by the amount of soluble CD40-L generated by a given number of cells over a period of time. A chimeric CD40-L of the present invention is cleaved at a rate at least 90% less than that of native CD40-L.

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences.

With respect all embodiments of the invention relating to nucleotide sequences, the percentage of sequence identity between one or more sequences may also be based on alignments using any suitable software such as the clustalW software (see world-wide website: ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB). Alternatively, nucleotide sequences may be analyzed using any suitable software such as DNASIS Max and the comparison of the sequences may be done at world-wide website: paralicin.orci/. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method are published in Rognes (2001). Default settings for score matrix and Gap penalties as well as E-values were used.

When referring to complementary sequences, the following base pairing rules can be applied, G pairs to C and U, A pairs to T and U. "Nucleic acid sequence" and "polynucleotide sequence" are interchangeable terms in the context of the present invention.

The term "vector" refers to a DNA molecule used as a vehicle to transfer recombinant genetic material into a host cell. The four major types of vectors are plasmids, bacteriophages and other viruses, cosmids, and artificial chromosomes. The vector itself is generally a DNA or RNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences. Simpler vectors called transcription vectors are only capable of being transcribed but not translated: they can be replicated in a target cell but not expressed, unlike expression vectors. Transcription vectors are used to amplify the inserted heterologous sequences. The transcripts may subsequently be isolated and used as templates suitable for in vitro translation systems. The choice of vector employed in embodiments of the present invention depends on the specific application of the vector encoding the polypeptides or polynucleotide of the invention. In some embodiments, the vector is a viral vector. In other embodiments, the vector is a non-viral vector.

The term "operatively linked" refers to the connection of elements being a part of a functional unit such as a gene or an open reading frame (e.g., encoding IFNβ). Accordingly, by operatively linking a promoter to a nucleic acid sequence encoding IFNβ the two elements become part of the functional unit—a gene. The linking of the expression control sequence (promoter) to the nucleic acid sequence enables the transcription of the nucleic acid sequence directed by the promoter. Expression control sequences can be linked to a nucleic acid sequence encoding IFNβ or CD40-L with an expression construct. For example, a nucleic acid sequence encoding IFNβ and CD40-L can both be under the control of the same expression control, i.e., a single copy of the expression control. Alternatively, each of the nucleic acid sequences encoding IFNβ and CD40-L can be under the control a separate expression control, i.e., a first copy of the expression control sequence controls the expression IFNβ and a second copy of the expression control sequence controls the expression of CD40-L. In some embodiments, a first expression control sequence controls the expression IFNβ and a second expression control sequence controls the expression of CD40-L, i.e., the two expression control sequences are different from each other.

Materials and Methods

Dendritic Cell Generation and peptide pool loading. DCs can be generated by suspending 7-11×$10^6$ PBMCs/mL in serum-free XVIVO-15 media (Lonza, Allendale, N.J.) followed by 3 hour culture in a 25 $cm^2$ cell culture flask (Corning, Corning, N.Y.). Cells can then be washed twice in PBS to remove non-adherent cells. Adherent cells can be cultured in serum-free X-VIVO media supplemented with 1000 units/ml each of GM-CSF and IL-4 (R&D Systems, Minneapolis, Minn.) for six days. DCs can then be collected, washed and counted. DCs can be loaded with the indicated peptide pool by incubating for one hour at 37° C. in 100 µl XVIVO-15 media supplemented with 1 µg/peptide/ml.

Dendritic cell transduction. Following plastic adherent generation, DCs can be re-suspended in 500 µL serum-free XVIVO-15 media supplemented with GM-CSF and IL-4 and transduced with 20,000 viral particles/cell of virus or viruses expressing IFNβ and CD40-L for 2 hours at 37° C. (25). After 2 hours, $2\times10^5$ DCs/well were seeded into 24 well plates and supplemented with 1.5 ml of complete culture media (XVIVO-15+10% human serum (SeraCare)+ Penicillin/Streptomycin) for an additional 24 hours.

Examples of embodiments of the invention include, but are not limited to:

Embodiment 1. An antigen presenting cell (APC) comprising a combination of an exogenous type I interferon and an exogenous CD40-L or one or more heterologous nucleic acid sequences encoding a combination of an exogenous type I IFN and an exogenous CD40-L.

Embodiment 2. The APC of embodiment 1, wherein:

a) the type I IFN is: IFNα comprising at least 80% sequence identity to the human IFNα (SEQ ID NO: 1), IFNβ comprising at least 80% sequence identity to the human IFNβ (SEQ ID NO: 2), IFNε comprising at least 80% sequence identity to the human IFNε (SEQ ID NO: 3), IFNκ comprising at least 80% sequence identity to the human IFNκ (SEQ ID NO: 4), or IFNω comprising at least 80% sequence identity to the human IFNω (SEQ ID NO: 5); and/or b) the CD40-L comprises at least 80% sequence identity to the human CD40-L (SEQ ID NO: 6), at least 80% sequence identity to a chimeric CD40-L having a sequence selected from SEQ ID NOs: 7 to 18, or at least 80% sequence identity to a chimeric CD40-L having a sequence of SEQ ID NO: 12; and/or c) the type I IFN is IFNβ comprising at least 80% sequence identity to the human IFNβ (SEQ ID NO: 2) and the CD40-L comprises at least 80% sequence identity to a chimeric CD40-L having a sequence of SEQ ID NO: 12.

Embodiment 3. The APC of embodiment 1 or 2, wherein the one or more heterologous nucleic acid sequences encoding the combination of type I IFN and CD40-L is in one or more viral constructs.

Embodiment 4. The APC of embodiment 3, wherein each of the one or more the viral constructs, independently, is an adenoviral construct, adeno-associated viral construct (AAV), poxvirus construct, lentiviral construct, alphaviral construct, herpesviral construct, retroviral construct, vaccinia viral construct, vesicular stomatitis viral construct, or herpes simplex viral construct.

Embodiment 5. The APC according to any of the preceding embodiments, wherein the APC is a human APC.

Embodiment 6. The APC according to any of the preceding embodiments, wherein the APC is a DC.

Embodiment 7. A composition comprising the APC of any one of the preceding embodiments and a pharmaceutically acceptable carrier.

Embodiment 8. The composition of embodiment 7, further comprising an adjuvant.

Embodiment 9. A method for treating a malignancy, comprising administering to a subject in need thereof an effective amount of APCs of any one of the preceding embodiments.

Embodiment 10. The method of embodiment 9, wherein the APCs are autologous cells.

Embodiment 11. The method of any one of embodiments 9 or 10, wherein the method further comprises administering to the subject one or more additional anti-cancer agents.

Embodiment 12. The method of any one of embodiments 9 to 11, wherein the method further comprises administering a chemotherapeutic drug (e.g., melphalan), immunomodulator, adjuvant, anemia drug (e.g., erythropoietin), radiation therapy, stem cell transplant, chimeric antigen receptor (CAR)-expressing T-cells (CAR T-cells), or a combination of two or more of the foregoing.

Embodiment 13. The method of embodiment any one of embodiments 9 to 12, comprising administering radiation therapy before administering the APCs.

Embodiment 14. The method of any one of embodiments 9 to 13, wherein the subject is human.

Embodiment 15. The method of any one of embodiments 9 to 14, wherein the APCs are administered by an intradermal injection, intra-tumoral injection, or an injection into a lymph node that drains into the tumor.

Embodiment 16. The method of embodiment 15, wherein the intradermal injection is at an anatomical site that drains to the axillary and/or inguinal lymph node basins of the subject.

Embodiment 17. The method of any one of embodiments 9 to 16, wherein the APCs are administered multiple times over a period of days.

Embodiment 18. The method of any one of embodiments 9 to 17, wherein the method further comprises conducting hematopoietic cell transplantation (hematopoietic stem cells or progenitor cells, e.g., from bone marrow, peripheral blood, or cord blood) on the subject.

Embodiment 19. The method of embodiment 18, wherein the hematopoietic cell transplant is autologous.

Embodiment 20. The method of embodiment 18 or 19, wherein the APCs are administered before and after the hematopoietic cell transplantation.

Embodiment 21. The method of any one of embodiments 18 to 20, further comprising conducting stem cell mobilization (e.g., using G-CSF) on the subject and collecting the hematopoietic cells from the subject prior to autologous hematopoietic cell transplantation.

Embodiment 22. The method of any one of embodiments 9 to 21, further comprising, prior to said administering APCs, collecting the APCs from the subject for production of the APCs to be administered to the subject.

Embodiment 23. The method of embodiment 22, wherein the APCs are cryopreserved prior to said administering.

Embodiment 24. The method of any one of embodiments 9 to 23, further comprising administering a chemotherapeutic agent (e.g., melphalan) before, during, or after said administering APCs.

Embodiment 25. The method of embodiment 24, further comprising administering a chemotherapeutic agent (e.g., melphalan) during the hematopoietic cell transplantation.

Embodiment 26. The method of any of embodiments 9 to 24, further comprising administering a checkpoint inhibitor to the subject.

Embodiment 27. The method of embodiment 26, wherein the checkpoint inhibitor is an inhibitor of: cytotoxic T-lymphocyte antigen 4 (CTLA4, also known as CD152), programmed cell death protein 1 (PD-1, also known as CD279) or programmed cell death 1 ligand 1 (PD-L1, also known as CD274).

Embodiment 28. The method of embodiment 27, wherein the inhibitor of CTLA4 is an antibody that binds CTLA4, the inhibitor of PD-1 is an antibody that binds PD-1, and the inhibitor of PD-L1 is an antibody that binds to PD-L1.

Embodiment 29. An oncolytic virus comprising a combination of a type I interferon and a CD40L or one or more nucleic acid sequences encoding a combination of a type I IFN and a CD40-L.

Embodiment 30. The oncolytic virus of embodiment 29, wherein:

a) the type I IFN is: IFNα comprising at least 80% sequence identity to the human IFNα (SEQ ID NO: 1), IFNβ comprising at least 80% sequence identity to the human IFNβ (SEQ ID NO: 2), IFNε comprising at least 80% sequence identity to the human IFNε (SEQ ID NO: 3), IFNκ comprising at least 80% sequence identity to the human IFNκ (SEQ ID NO: 4), or IFNω comprising at least 80% sequence identity to the human IFNω (SEQ ID NO: 5); and/or b) the CD40-L comprises at least 80% sequence identity to the human CD40-L (SEQ ID NO: 6), or at least 80% sequence identity to a chimeric CD40-L having a sequence selected from SEQ ID NOs: 7 to 18; and/or c) the type I IFN is IFNβ comprising at least 80% sequence identity to the human IFNβ (SEQ ID NO: 2) and the CD40-L comprises at least 80% sequence identity to a chimeric CD40-L having a sequence of SEQ ID NO: 12.

Embodiment 31. The oncolytic virus of any of embodiments 29-30, wherein oncolytic virus is adenovirus, reovirus, herpes virus, picornavirus (e.g., coxsackievirus, poliovirus, and Seneca Valley virus), paramyxovirus (e.g., measles virus and Newcastle disease virus), parvovirus, rhabdovirus (e.g., vesicular stomatitis virus), vaccinia virus, poxvirus, Sindbis virus, myxoma virus, Maraba virus, influenza virus, mumps virus, arenavirus, vaccinia virus, or recombinant adenovirus containing a E1A delta-24 deletion, E1b-55K deletion, and E3 region deletion.

Embodiment 32. A composition comprising the oncolytic virus of any one of embodiments 29-31 and a pharmaceutically acceptable carrier.

Embodiment 33. The composition of embodiment 32, further comprising an adjuvant.

Embodiment 34. A method for treating a malignancy, comprising administering to a subject in need thereof an effective amount of an oncolytic virus of any one of embodiments 29-31 or the composition of embodiment 31 or 32.

Embodiment 35. The method of embodiment 34, wherein the method further comprises administering one or more additional anti-cancer agents to the subject.

Embodiment 36. The method of embodiment 35, wherein the method further comprises administering a chemotherapeutic drug (e.g., melphalan), immunomodulator, adjuvant, anemia drug (e.g., erythropoietin), radiation therapy, stem cell transplant, chimeric antigen receptor (CAR)-expressing T-cells (CAR T-cells), or a combination of two or more of the foregoing.

Embodiment 37. The method of any one of embodiments 34 to 36, wherein the subject is human.

Embodiment 38. The method of any one of embodiments 34 to 37, wherein the oncolytic virus is administered multiple times over a period of days.

Embodiment 39. The method of any one of embodiments 34 to 38, wherein the oncolytic virus is administered by an intradermal injection, intra-tumoral injection, intravenous injection, or an injection into a lymph node that drains into the tumor.

Embodiment 40. The method of embodiment 39, wherein the intradermal injection is at an anatomical site that drains to the axillary and/or inguinal lymph node basins of the subject.

Embodiment 41. The method of any one of embodiments 34 to 40, wherein the method further comprises conducting hematopoietic cell transplantation (hematopoietic stem cells or progenitor cells, e.g., from bone marrow, peripheral blood, or cord blood) on the subject.

Embodiment 42. The method of embodiment 41, wherein the hematopoietic cell transplant is autologous.

Embodiment 43. The method of embodiment 41 or 42, wherein the oncolytic virus is administered before and after the hematopoietic cell transplantation.

Embodiment 44. The method of any one of embodiments 34 to 43, further comprising conducting stem cell mobilization (e.g., using G-CSF) on the subject and collecting the hematopoietic cells from the subject prior to autologous hematopoietic cell transplantation.

Embodiment 45. The method of any one of embodiments 34 to 44, further comprising administering a chemotherapeutic agent (e.g., melphalan) before, during, or after administering the oncolytic virus.

Embodiment 46. The method of any of embodiments 43 to 45, further comprising administering a chemotherapeutic agent (e.g., melphalan) during the hematopoietic cell transplantation.

Embodiment 47. The method of any of embodiments 34 to 46, further comprising administering a checkpoint inhibitor to the subject.

Embodiment 48. The method of embodiment 47, wherein the checkpoint inhibitor is an inhibitor of: cytotoxic T-lymphocyte antigen 4 (CTLA4, also known as CD152), programmed cell death protein 1 (PD-1, also known as CD279) or programmed cell death 1 ligand 1 (PD-L1, also known as CD274).

Embodiment 49. The method of embodiment 48, wherein the inhibitor of CTLA4 is an antibody that binds CTLA4, the inhibitor of PD-1 is an antibody that binds PD-1, and the inhibitor of PD-L1 is an antibody that binds to PD-L1.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Figure 2:
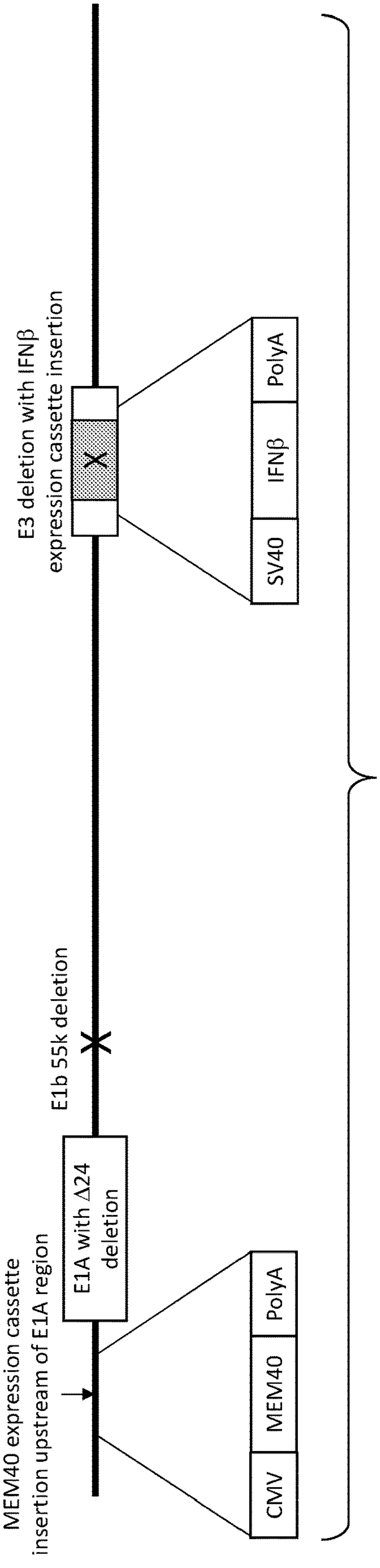
FIG. 2 shows a schematic construction of an oncolytic adenovirus with dual expression cassettes encoding CD40-L and IFNβ.

Example 1—Construction of Dual Expression Cassette MEM40 and IFNβ Oncolytic Adenovirus An oncolytic adenovirus type 5 was constructed with an expression cassette for MEM40 that includes a CMV promoter, MEM40 nucleotide sequence, and polyadenylation sequence. The expression cassette was inserted upstream of the adenovirus E1A gene region containing a 24 nucleotide deletion. In addition, a second expression cassette for IFNβ that includes an SV40 promoter, IFNβ nucleotide sequence, and polyadenylation sequence was inserted in the adenovirus genome location where adenovirus E3 region was deleted. The E1b 55k region of the adenovirus genome has also been deleted. FIG. 2 shows a schematic construction of the exemplified oncolytic adenovirus with dual expression cassettes encoding CD40-L and IFNβ.

Figure 3:
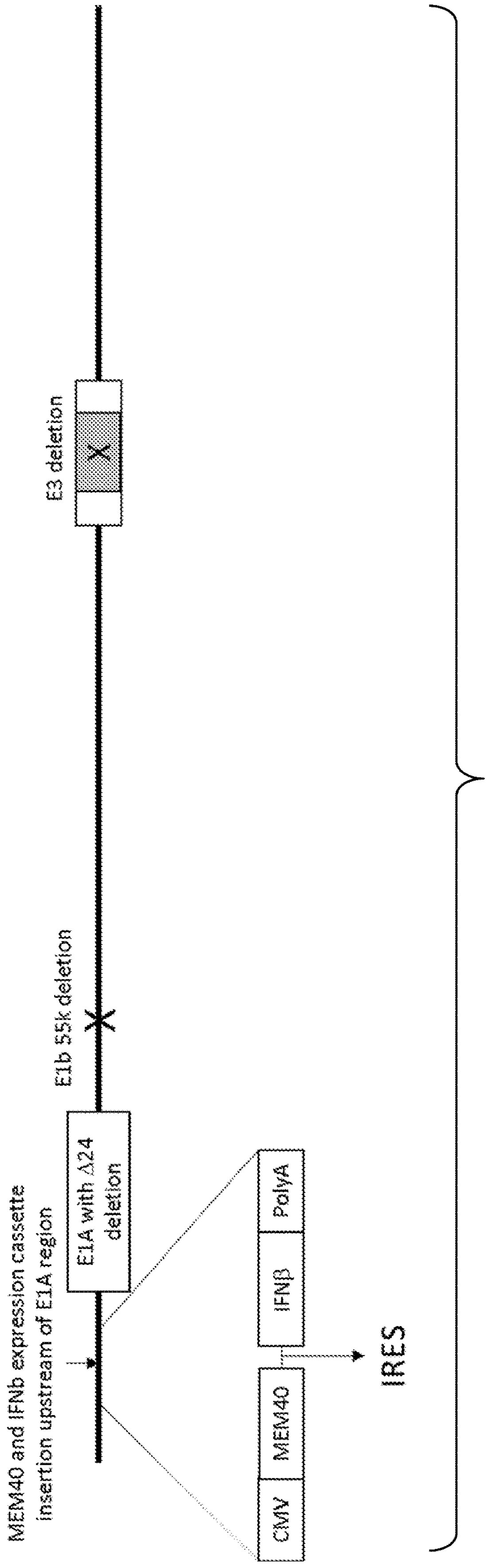
FIG. 3 shows a schematic construction of an oncolytic virus with a single expression cassette encoding CD40-L and IFNβ separated by an internal ribosome entry site (IRES).

Example 2—Construction of Single Expression Cassette MEM40 and IFNβ Oncolytic Adenovirus An oncolytic adenovirus type 5 was constructed with an expression cassette for MEM40 and IFNβ that includes a CMV promoter, MEM40 and IFNβ nucleotide sequences separated by an internal ribosome entry site, and polyadenylation sequence. The expression cassette was inserted upstream of the adenovirus E1A gene region containing a 24 nucleotide deletion. The adenovirus contains E3 and E1b 55k region deletions. FIG. 3 shows a schematic construction of the exemplified oncolytic virus with a single expression cassette encoding CD40-L and IFNβ separated by an internal ribosome entry site (IRES).

Example 3—Oncolytic Activity of a Virus Expressing IFNβ and MEM40

Figure 4B:
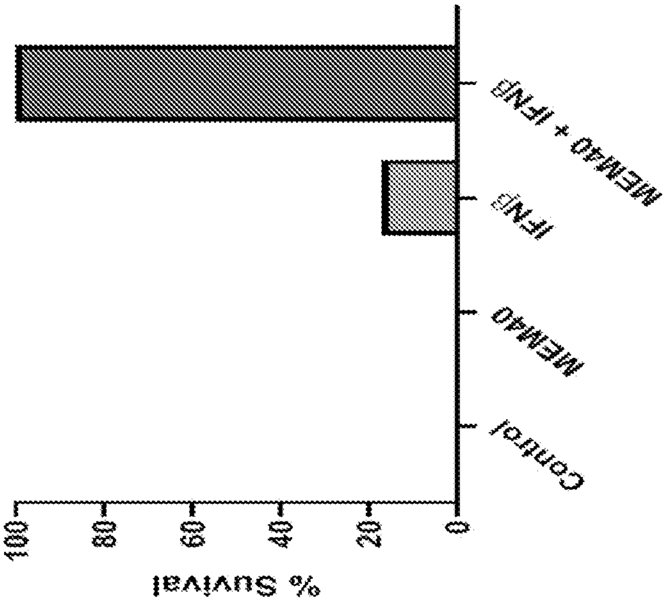
FIGS. 4A-4B show the tumor growth and survival of mice having an aggressive B16 sub-cutaneous melanoma tumor. Control untreated mice (n=5), mice injected with Dendritic cells expressing IFNβ (IFNβ) (n=6), Adenovirus-MEM40 (MEM40) (n=6) and dual agent administration (n=5) are indicated. Adenovirus-MEM40 ($10^{10}$ viral particles per tumor) was injected on the same days as DCs as indicated. Mean tumor growth is shown in (A) and mouse survival (36 days after tumor implantation) in (B). Combination treatment with DC-IFNβ and Ad-MEM40 significantly reduced tumor growth compared to other treatment arms (t-test; $p<0.05$).
Figure 4A:
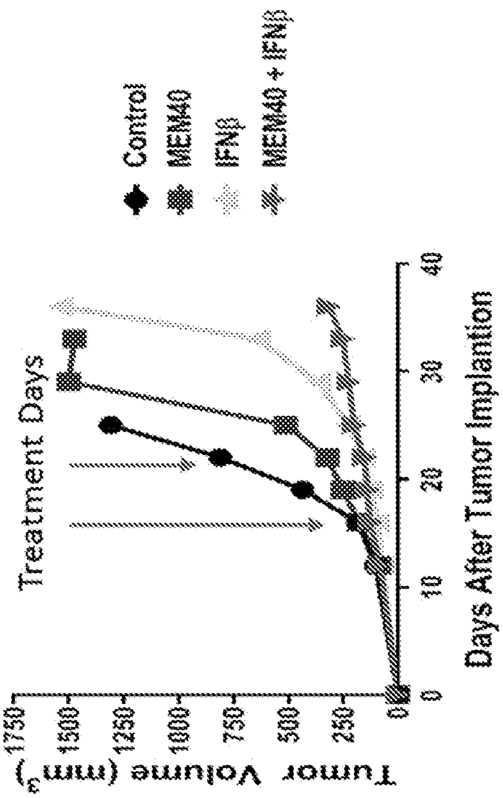

The individual and combined effect of IFNβ and MEM40 expression on the tumor growth of mice having an aggressive B16 sub-cutaneous melanoma was tested. Dendritic cells expressing IFNβ ($10^6$ cells transduced with a lentivirus expressing IFNβ) and replication-deficient adenovirus expressing MEM40 (Ad-MEM40, $10^{10}$ viral particles) were injected in tumors as indicated in FIG. 4A. Importantly, compared to either agent alone, the combined treatment significantly reduced tumor growth (FIG. 4A). As shown in FIG. 4B, following the treatment with both agents, all of the mice implanted with the aggressive B16 melanoma tumor cells were alive at the completion of experiment. In contrast, following the treatment with Ad-MEM40, none of the mice implanted with the B16 melanoma tumor cells were alive at the completion of the experiment; and following the treatment with DC expressing only IFNβ, only 17% of the mice implanted with the B16 melanoma tumor cells were alive at the completion of the experiment.

Adenovirus (Δ24) expressing MEM40 and/or IFNβ were tested for their oncolytic ability in various cancer models. MEM-188 refers to an adenovirus Δ24 expressing MEM40 only, and MEM-288 refers to an adenovirus Δ24 expressing both MEM40 and IFNβ. In A549 lung tumor cells, MEM-288 exhibits 7 and 100 times greater tumor killing and immune activation, respectively, compared to a control oAdv and MEM-188. For example, FIG. 5A shows that infection in A549 lung tumor cells with increasing doses of MEM-288 resulted in a very low cell viability of about 5%. An $LD_{50}$ of 26 multiplicity of infection (MOI) was obtained for MEM-288. In contrast, infection in A549 lung tumor cells with increasing doses of MEM-188 resulted in a somewhat higher cell viability of about 15% and a much higher $LD_{50}$ of 194 MOI. A control oAdv did not show significant cell killing property. For these experiments, cell viability was determined by luciferase activity assay.

Figure 5B:
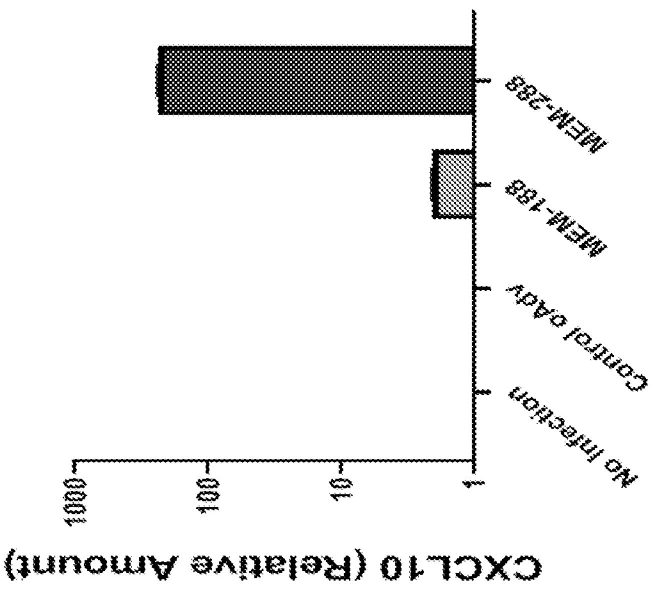
FIGS. 5A-5B show that an oncolytic adenovirus expressing MEM40 and IFNβ (MEM-288) exhibits 7 and 100 times greater tumor killing and immune activation properties, respectively, compared to an oncolytic virus expressing only MEM40 (MEM-188) and a control oncolytic adenovirus (control oAdv, an unarmed adenovirus).
Figure 5A:
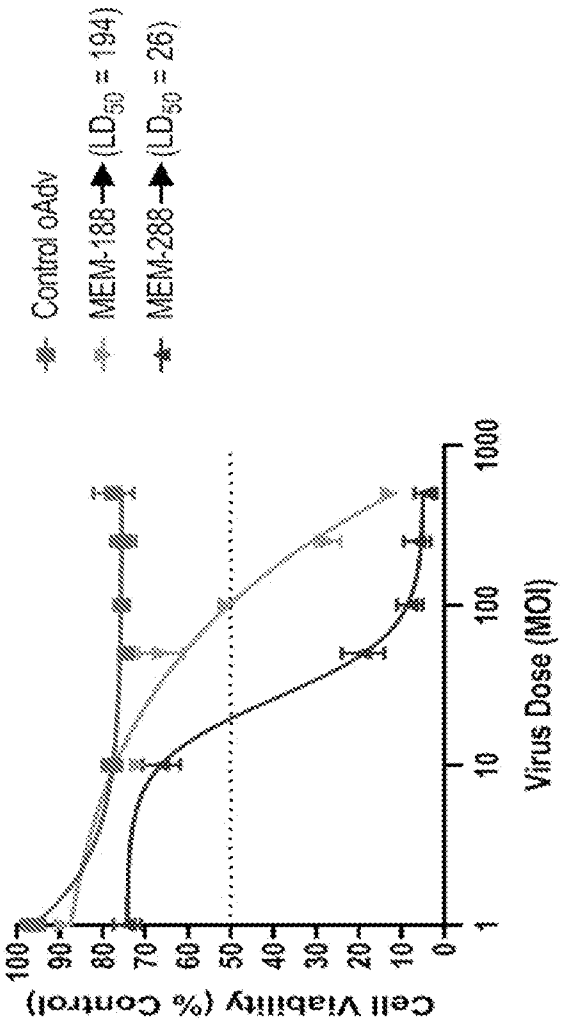

Downstream target of IFNβ CXCL10 was determined by qRT-PCR after 48 hours infection with MEM-188, MEM-288 or a control oAdv (FIG. 5B). FIG. 5B shows that in about 48 hours after infection with MEM-288, the expression of CXCL10, which is an interferon inducible chemokine and a T-cell activator, increased by about 200 to 300 times. Infection with a control oAdv showed no such increase and infection with MEM-188 showed a moderate increase of about 2 to 3 times.

Figure 6A:
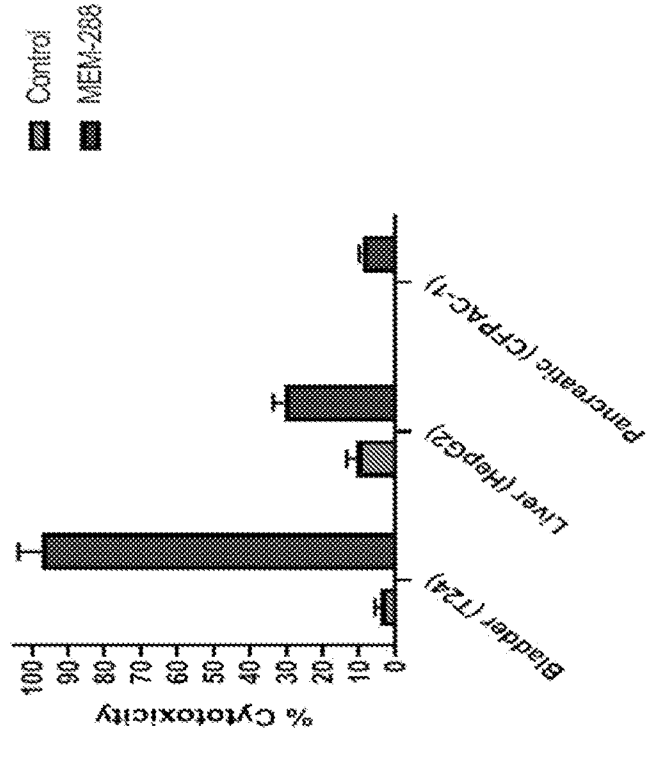
FIGS. 6A-6B show that an oncolytic adenovirus expressing MEM40 and IFNβ (MEM-288) is effective in killing multiple tumor types and oncogene driven cancers. (A) Comparison with control oncolytic adenovirus in killing human bladder, liver, and pancreatic tumors and (B) comparison with an oncolytic adenovirus expressing only MEM40 (MEM-188) in killing KRAS mutant lung tumor (HCC44 cell line).

FIG. 6A shows that MEM-288 is broadly active against several tumor types. Different carcinoma tumor types were infected with MEM-288 (blue) or control oAdv (grey) and cell death was analyzed after 48 hours. Infection with MEM-288 provided a significantly higher cytotoxicity compared to infection with a control oAdv.

Figure 6B:
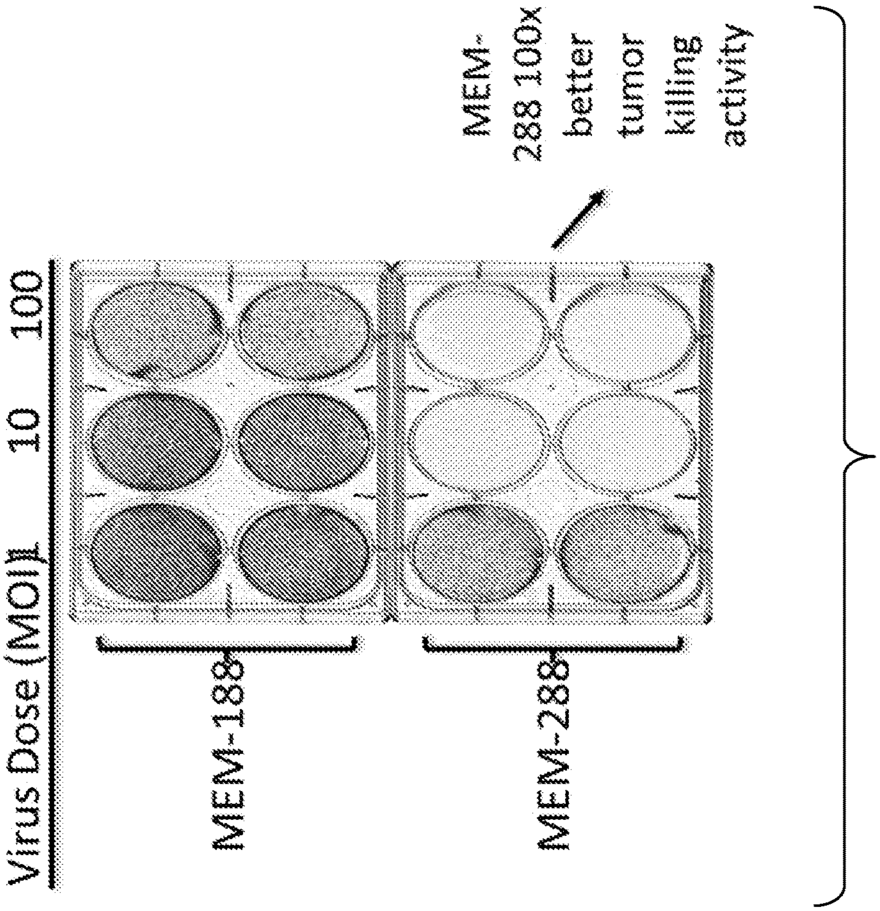
Figure 10:
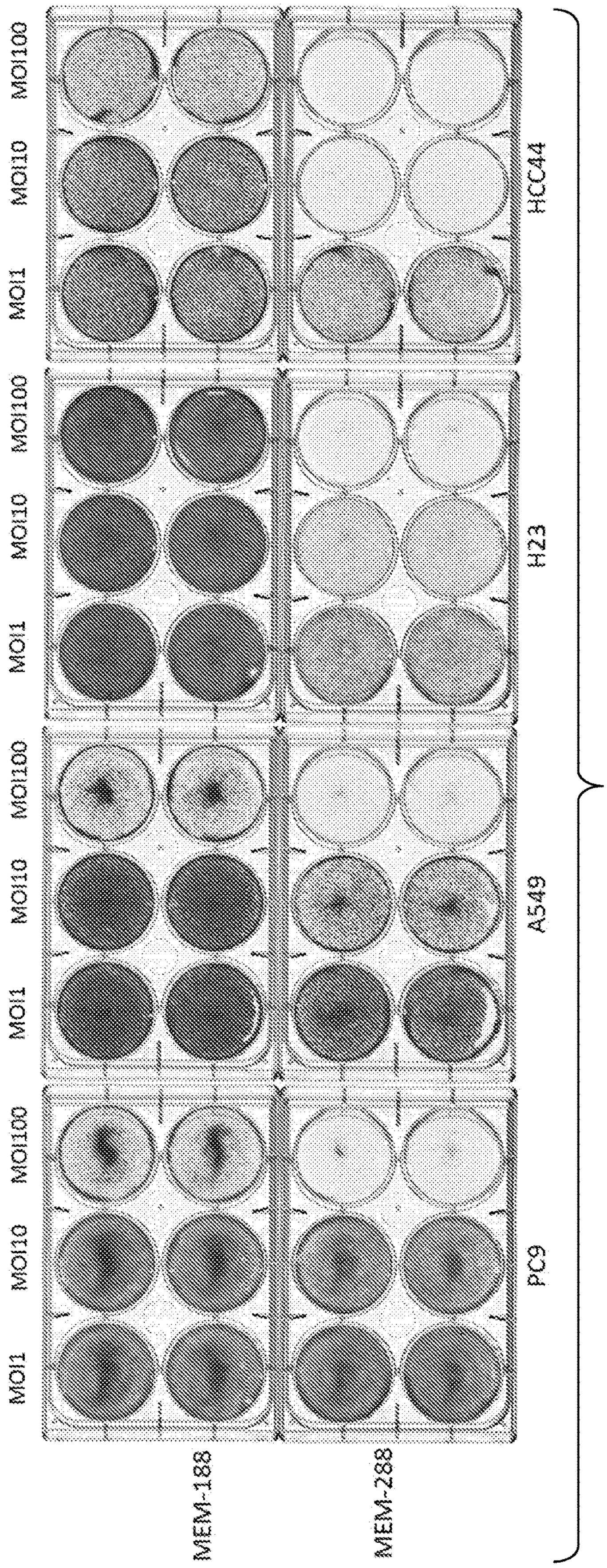
FIG. 10 shows enhanced oncolytic capacity in several cancer cell lines following infection with an oncolytic adenovirus expressing MEM40 and IFNβ (MEM-288), compared to an oncolytic virus expressing only MEM40 (MEM-188). Cells were stained with crystal violet 3 days after infection.

KRAS mutant lung tumor (HCC44 cell line), an example of the most common oncogenic driven mutant form of lung adenocarcinoma, was infected with increasing doses of MEM-188 and MEM-288. Cell viability was measured by crystal violet staining (purple=viable; clear=dead). FIG. 6B shows that compared to MEM-188, MEM-288 was approximately 100 times more effective in killing this tumor cell line. Similar results were observed with additional lung tumor cell lines (FIG. 10).

Figure 7:
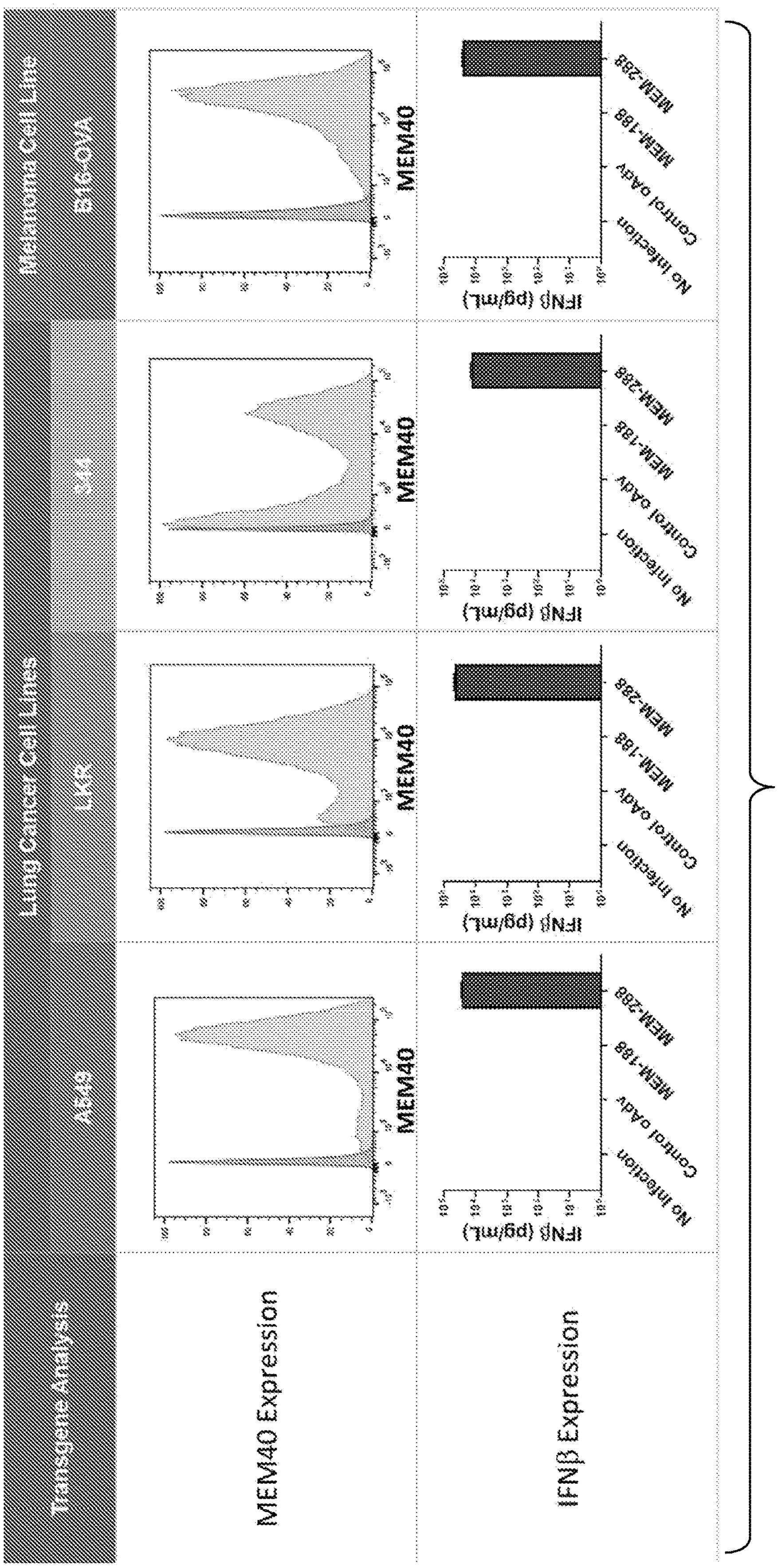
FIG. 7 shows dual transgene expression of MEM40 and IFNβ by an oncolytic adenovirus expressing MEM40 and IFNβ (MEM-288) in multiple cell lines.

In vitro expression of MEM40 and IFNβ in different tumor cell lines was tested, and results are shown in FIG. 7. Cells were infected with MEM-288 at MOI of 250 for 2 days. MEM40 expression was determined by fluorescent activated cell sorting (FACS) in human A549 lung cancer line, mouse lung cancer LKR and 344 lines, and mouse B16-OVA melanoma cell line while IFNβ expression was determined by an ELISA assay. All cell lines expressed detectable cell surface expression of MEM40 and release of IFNβ into the culture supernatant.

Figure 8:
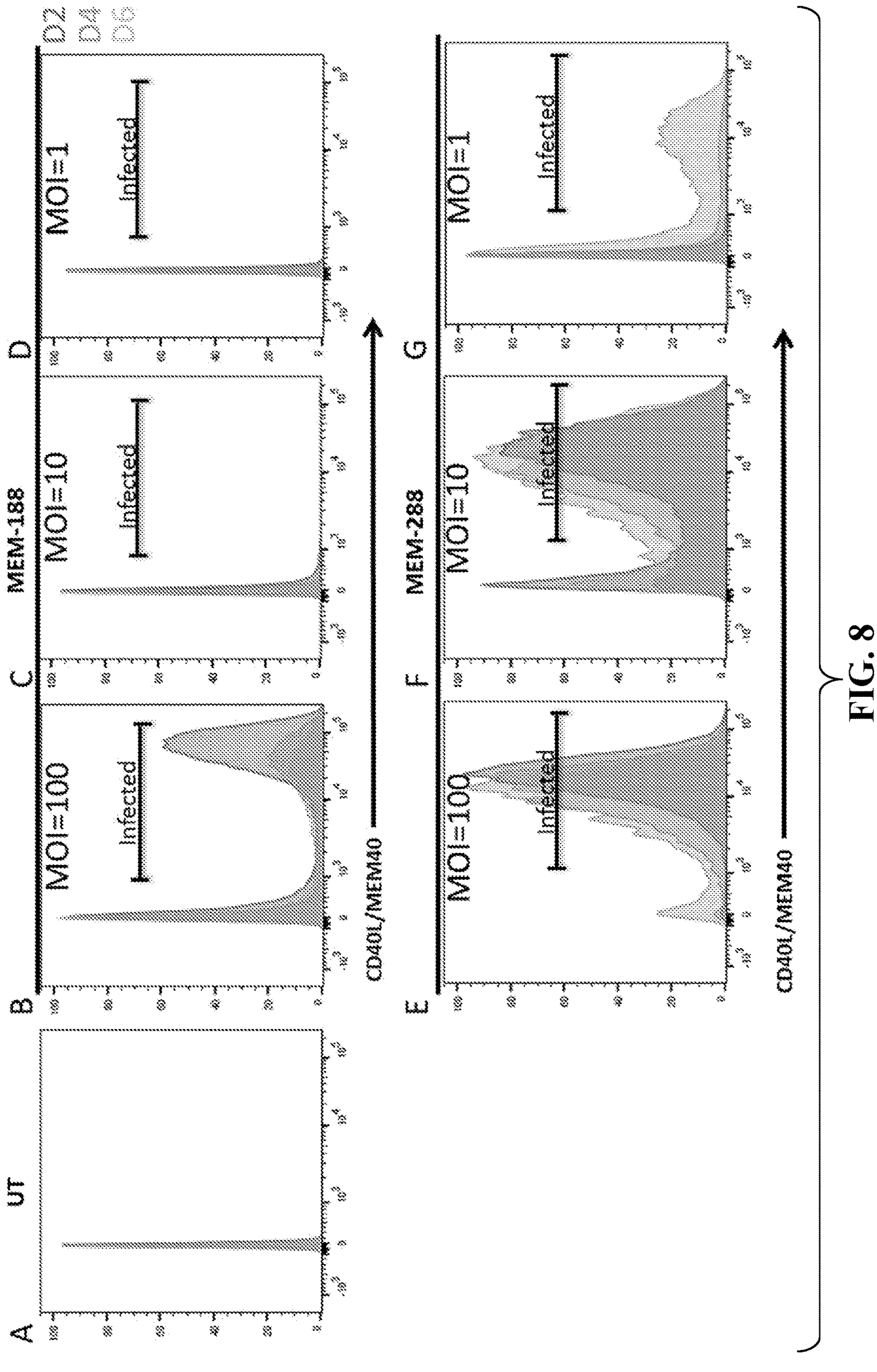
FIG. 8 shows enhanced transgene expression and replication of an oncolytic virus expressing MEM40 and IFNβ. Comparison of MEM40 expression after infection with MEM-188 and MEM-288 in A549 cell line is shown. Cells were infected with/without oncolytic MEM-188 or MEM-288 at different MOIs for 2, 4 and 6 days. MEM40 expression was determined by FACS. For the FACS results: Red line—Day 2, Blue line—Day 4 and Orange line—Day 6. (A): uninfected cells. (B): MEM-188 MOI=100. (C): MEM-188 MOI=10. (D): MEM-188 MOI=1. (E): MEM-288 MOI=100. (F): MEM-288 MOI=10. (G): MEM-288 MOI=1.
Figure 9:
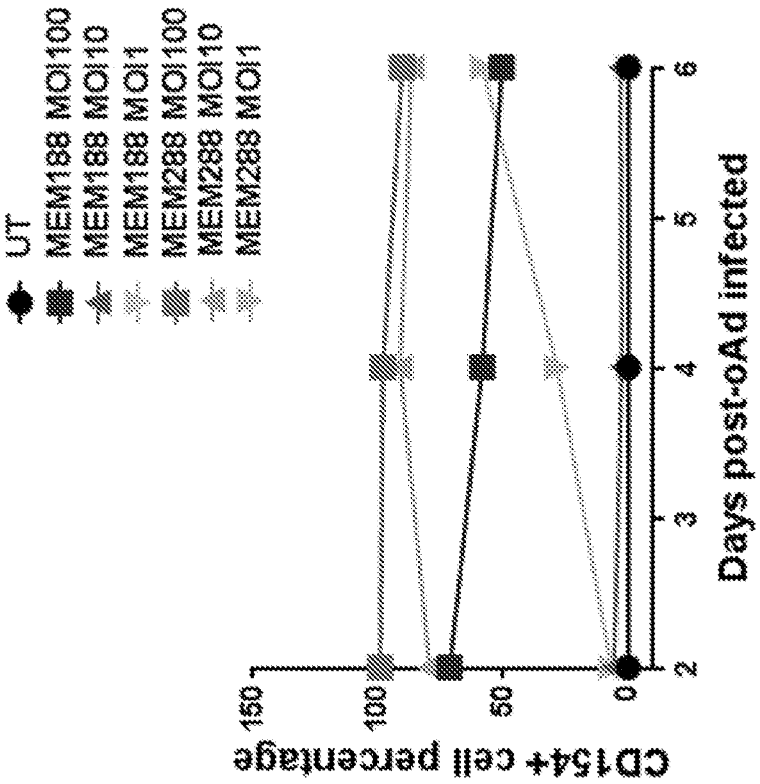
FIG. 9 shows the comparison of MEM40 expression in the A549 lung tumor cell line after infection with an oncolytic adenovirus expressing MEM40 and IFNβ (MEM-288) compared to an oncolytic virus expressing only MEM40 (MEM-188).

FIG. 8 shows enhanced transgene expression and replication of MEM-288 infected in human lung cancer cell line A549. In this experiment, A549 were not infected (A) or infected with indicated MOI of MEM-188 (B-D) or MEM-288 (E-G). MEM40 expression was detected by flow cytometry using an antibody against mouse CD40L. MEM40 expression was detected on days 2, 4 and 6 after infection of both viruses at the different MOI as indicated. MEM40 expression following infection with MEM-188 was high on day 2 but substantially diminished by day 6 (FIG. 8B). In contrast, MEM-288 infected cells retained high MEM40 expression on days 4 and 6 (FIG. 8E). At an MOI of 10, MEM40 expression was readily detected in MEM-288 (FIG. 8F) infected cells but not in MEM-188 infected cells (FIG. 8C). After MEM-288 infection at MOI of 1, MEM40 temporally increased from low to high expression on days 2, 4, and 6, respectively (FIG. 8G). No such change occurred in MEM-188 infected cells ((FIG. 8D). This result indicates that MEM-288 has substantially higher replicative activity compared to MEM-188. The expression of MEM40 after infection with MEM-188 or MEM-288 in the A549 cell line from results in FIG. 8 are plotted and shown in FIG. 9.

Figure 11:
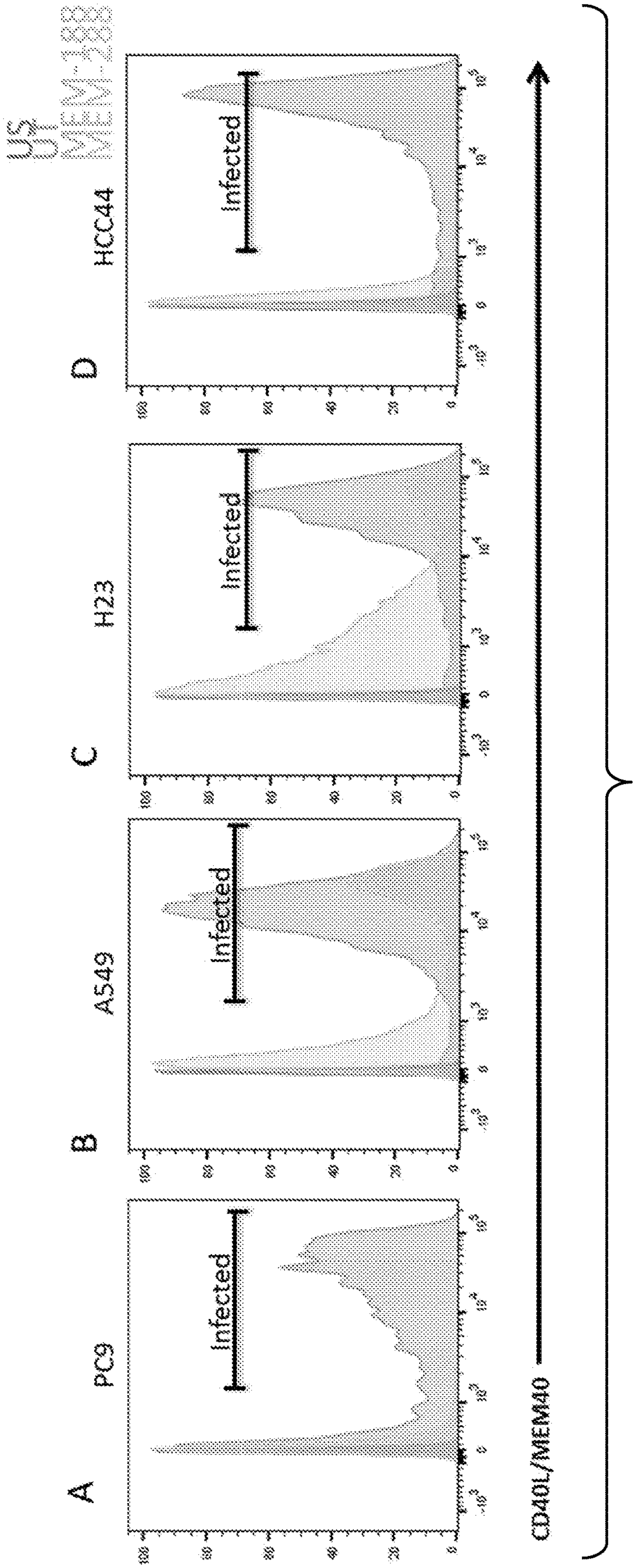
FIG. 11 shows enhanced expression of MEM40 in several cancer cell lines after infection with an oncolytic adenovirus expressing MEM40 and IFNβ (MEM-288) compared to an oncolytic virus expressing only MEM40 (MEM-188). Cells were infected with/without oncolytic MEM-188 or MEM-288 at MOI=100 for 3 days. MEM40 expression was determined by FACS in (A) PC9, (B) A549, (C) H23 and (D) HCC44 cell lines. For the FACS results: Red line=unstained, Blue line=untreated, Green line=MEM-188, Orange line=MEM-288.

Oncolytic ability of MEM-288 was tested in various lung cancer cell lines. Cells were infected with MEM-188 or MEM-288 at different MOIs for 3 days. Cell viability was determined by cell counting assay and crystal violet assay in PC9, A549, H23, and HCC44 cell lines. MEM-288 shows higher cell killing ability at MOI of 10 and 100 against all of these cell lines (FIG. 10). Expression of MEM40 in cell lines shown in FIG. 10 is shown in FIG. 11. Cells were infected with/without oncolytic MEM-188 or MEM-288 at MOI=100 for 3 days, after which MEM40 expression was found to be substantially higher in MEM-288 infected cells.

Figure 12:
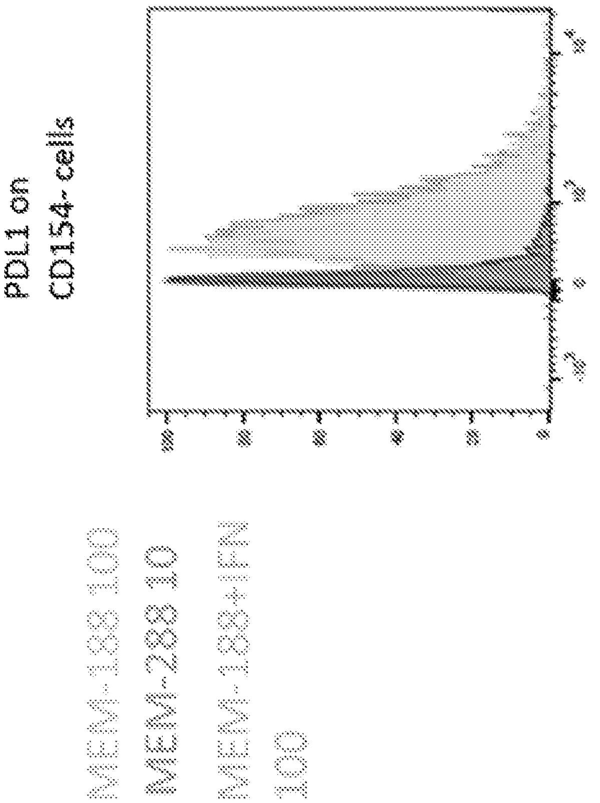
FIG. 12 shows expression of PDL1 in A549 cell line bystander cells not infected with adenovirus. Cells were infected with/without oncolytic MEM-188 or MEM-288 at different MOIs as indicated for 3 days. MEM-188 infection was also combined with exogenous IFNβ addition as indicated. PDL1 expression was determined by FACS specifically in cells not expressing MEM40 (i.e. uninfected).

FIG. 12 shows that cells in a mixed culture of infected and non-infected cells with MEM-288, the bystander non-infected cells upregulate PDL1 expression. MEM-188 infection did not upregulate PDL1 expression in bystander cells unless exogenous IFNβ was added. Therefore, IFNβ increases PDL1 expression in bystander non-infected cells upon MEM-288 infection.

Figure 13:
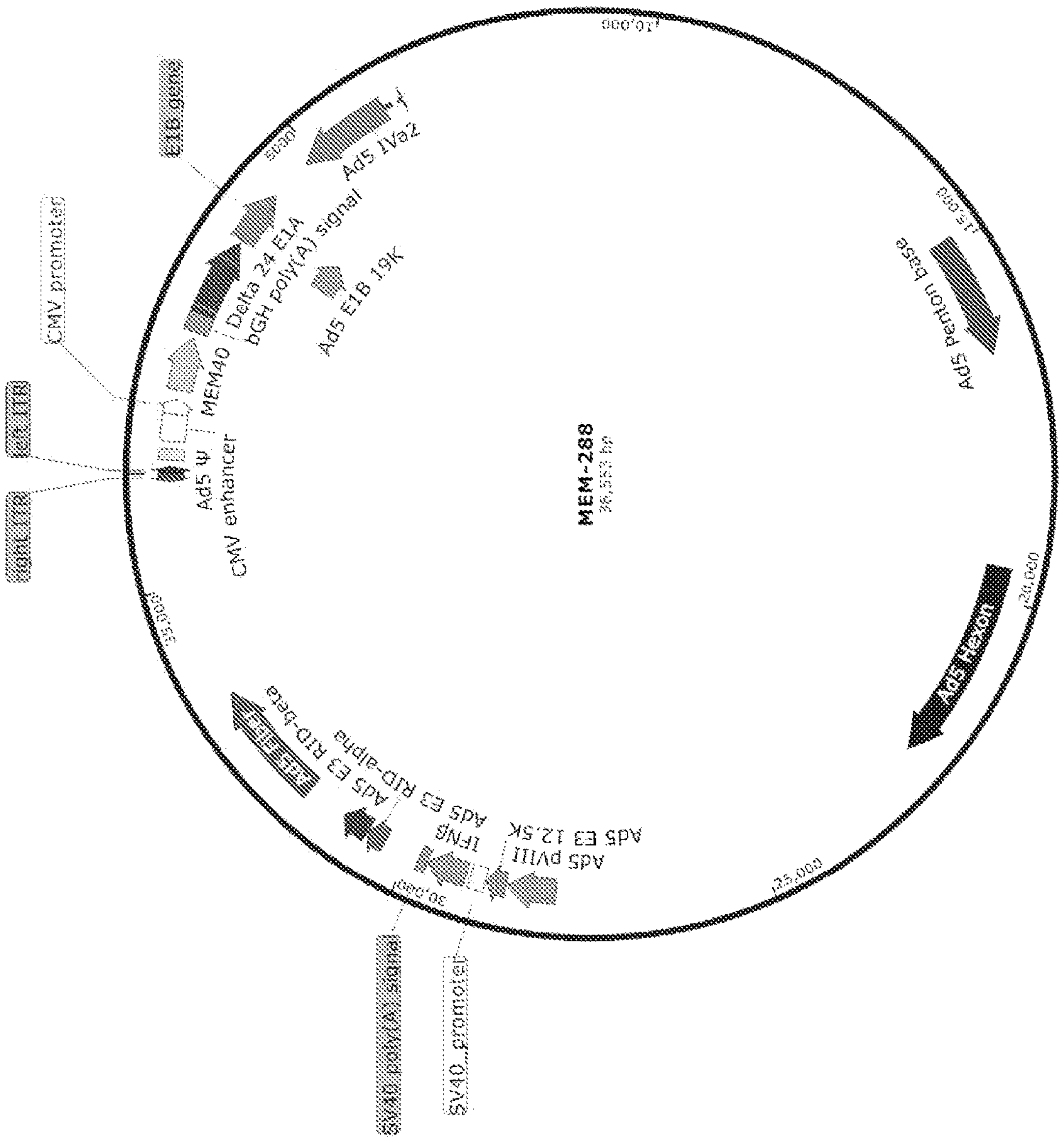
FIG. 13 shows an example of a vector map depicting an oncolytic adenovirus expressing MEM40 and IFNβ (MEM-288).

FIG. 13 shows the viral vector map of MEM-288, and oncolytic adenovirus (Δ24) expressing MEM40 and/or IFNβ.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An oncolytic virus comprising:

(i) a nucleic acid sequence encoding a type I interferon, wherein the type I interferon is: IFNα comprising at least 80% sequence identity to the human IFNα (SEQ ID NO: 1), IFNβ comprising at least 80% sequence identity to the human IFNβ (SEQ ID NO: 2), IFNε comprising at least 80% sequence identity to the human IFN& (SEQ ID NO: 3), IFNκ comprising at least 80% sequence identity to the human IFNκ (SEQ ID NO: 4), or IFNω comprising at least 80% sequence identity to the human IFN (SEQ ID NO: 5);

(ii) a nucleic acid sequence encoding a CD40-L, which comprises at least 80% sequence identity to a chimeric CD40-L having a sequence selected from SEQ ID NOs: 7 to 18;

(iii) a CMV promoter sequence operatively linked to the nucleic acid sequence encoding the CD40L such that expression of the CD40L is directed by the CMV promoter; and (iv) an SV40 promoter sequence operatively linked to the nucleic acid sequence encoding the type I interferon such that expression of the type I interferon is directed by the SV40 promoter, wherein the oncolytic virus is recombinant adenovirus.

2. The oncolytic virus of claim 1, wherein:

the type I interferon is IFNβ comprising at least 80% sequence identity to the human IFNβ (SEQ ID NO: 2) and the CD40-L comprises at least 80% sequence identity to a chimeric CD40-L having a sequence of SEQ ID NO: 12.

3. A composition comprising the oncolytic virus of claim 1; and a pharmaceutically acceptable carrier.

4. The composition of claim 3, further comprising an adjuvant.

5. A method for treating a malignancy, comprising administering to a subject in need thereof an effective amount of the oncolytic virus of claim 1.

6. The method of claim 5, wherein the method further comprises administering one or more additional anti-cancer agents to the subject.

7. A method for treating a malignancy, comprising:

(i) administering to a subject in need thereof an effective amount of the oncolytic virus of claim 1; and (ii) conducting hematopoietic cell transplantation on the subject.

8. The oncolytic virus of claim 1, wherein the nucleic acid sequence encoding a type I interferon was inserted at a deleted adenovirus E3 region and the nucleic acid sequence encoding a CD40-L was inserted upstream of the adenovirus E1A gene region containing a 24 nucleotide deletion.

* * * * *

```
                              SEQUENCE LISTING


<160> NUMBER OF SEQ ID NOS: 30

<210> SEQ ID NO 1
<211> LENGTH: 189
<212> TYPE: PRT
<213> ORGANISM: Homo sapiens

<400> SEQUENCE: 1

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

His Phe Ser Cys Leu Lys Asp Arg His Asp Phe Gly Phe Pro Glu Glu
    50                  55                  60

Glu Phe Asp Gly His Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185


<210> SEQ ID NO 2
<211> LENGTH: 187
<212> TYPE: PRT
<213> ORGANISM: Homo sapiens

<400> SEQUENCE: 2

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80
```

-continued

```
Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185


<210> SEQ ID NO 3
<211> LENGTH: 208
<212> TYPE: PRT
<213> ORGANISM: Homo sapiens

<400> SEQUENCE: 3

Met Ile Ile Lys His Phe Phe Gly Thr Val Leu Val Leu Leu Ala Ser
1               5                   10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205


<210> SEQ ID NO 4
<211> LENGTH: 207
<212> TYPE: PRT
<213> ORGANISM: Homo sapiens

<400> SEQUENCE: 4

Met Ser Thr Lys Pro Asp Met Ile Gln Lys Cys Leu Trp Leu Glu Ile
1               5                   10                  15
```

-continued

```
Leu Met Gly Ile Phe Ile Ala Gly Thr Leu Ser Leu Asp Cys Asn Leu
            20                  25                  30

Leu Asn Val His Leu Arg Arg Val Thr Trp Gln Asn Leu Arg His Leu
        35                  40                  45

Ser Ser Met Ser Asn Ser Phe Pro Val Glu Cys Leu Arg Glu Asn Ile
    50                  55                  60

Ala Phe Glu Leu Pro Gln Glu Phe Leu Gln Tyr Thr Gln Pro Met Lys
65                  70                  75                  80

Arg Asp Ile Lys Lys Ala Phe Tyr Glu Met Ser Leu Gln Ala Phe Asn
                85                  90                  95

Ile Phe Ser Gln His Thr Phe Lys Tyr Trp Lys Glu Arg His Leu Lys
            100                 105                 110

Gln Ile Gln Ile Gly Leu Asp Gln Gln Ala Glu Tyr Leu Asn Gln Cys
        115                 120                 125

Leu Glu Glu Asp Lys Asn Glu Asn Glu Asp Met Lys Glu Met Lys Glu
    130                 135                 140

Asn Glu Met Lys Pro Ser Glu Ala Arg Val Pro Gln Leu Ser Ser Leu
145                 150                 155                 160

Glu Leu Arg Arg Tyr Phe His Arg Ile Asp Asn Phe Leu Lys Glu Lys
                165                 170                 175

Lys Tyr Ser Asp Cys Ala Trp Glu Ile Val Arg Val Glu Ile Arg Arg
            180                 185                 190

Cys Leu Tyr Tyr Phe Tyr Lys Phe Thr Ala Leu Phe Arg Arg Lys
        195                 200                 205


<210> SEQ ID NO 5
<211> LENGTH: 195
<212> TYPE: PRT
<213> ORGANISM: Homo sapiens

<400> SEQUENCE: 5

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175
```

```
Leu Ser Thr Asn Met Gln Glu Arg Leu Arg Ser Lys Asp Arg Asp Leu
            180                 185                 190

Gly Ser Ser
        195


<210> SEQ ID NO 6
<211> LENGTH: 261
<212> TYPE: PRT
<213> ORGANISM: Homo sapiens

<400> SEQUENCE: 6

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 7
<211> LENGTH: 260
<212> TYPE: PRT
<213> ORGANISM: Artificial sequence
<220> FEATURE:
<223> OTHER INFORMATION: chimeric CD40-L

<400> SEQUENCE: 7

Met Ile Glu Thr Tyr Ser Gln Pro Ser Pro Arg Ser Val Ala Thr Gly
1               5                   10                  15
```

```
Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 8
<211> LENGTH: 252
<212> TYPE: PRT
<213> ORGANISM: Artificial sequence
<220> FEATURE:
<223> OTHER INFORMATION: chimeric CD40-L

<400> SEQUENCE: 8

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110
```

-continued

```
Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Val His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 9
<211> LENGTH: 260
<212> TYPE: PRT
<213> ORGANISM: Artificial sequence
<220> FEATURE:
<223> OTHER INFORMATION: chimeric CD40-L

<400> SEQUENCE: 9

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220
```

-continued

```
Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 10
<211> LENGTH: 252
<212> TYPE: PRT
<213> ORGANISM: Artificial sequence
<220> FEATURE:
<223> OTHER INFORMATION: chimeric CD40-L

<400> SEQUENCE: 10

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Val His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 11
<211> LENGTH: 260
<212> TYPE: PRT
<213> ORGANISM: Artificial sequence
<220> FEATURE:
<223> OTHER INFORMATION: chimeric CD40-L

<400> SEQUENCE: 11

Met Ile Glu Thr Tyr Ser Gln Pro Ser Pro Arg Ser Val Ala Thr Gly
1               5                   10                  15
```

```
Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260
```

<210> SEQ ID NO 12
<211> LENGTH: 252
<212> TYPE: PRT
<213> ORGANISM: Artificial sequence
<220> FEATURE:
<223> OTHER INFORMATION: chimeric CD40-L

<400> SEQUENCE: 12

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110
```

-continued

```
Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Ile His Leu Gly Gly Val Phe Glu Leu Gln Pro
210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 13
<211> LENGTH: 260
<212> TYPE: PRT
<213> ORGANISM: Artificial sequence
<220> FEATURE:
<223> OTHER INFORMATION: chimeric CD40-L

<400> SEQUENCE: 13

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Ala Ser Ser Gln Ala Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ala Lys Pro Cys Gly Gln Gln Ser Ile His Leu
    210                 215                 220
```

Gly Gly Val Phe Glu Leu Gln Pro Gly Ala Ser Cys Phe Val Asn Val
225 230 235 240

Thr Asp Pro Ser Gln Val Ser His Gly Thr Gly Phe Thr Ser Phe Gly
245 250 255

Leu Leu Lys Leu
260

<210> SEQ ID NO 14
<211> LENGTH: 252
<212> TYPE: PRT
<213> ORGANISM: Artificial sequence
<220> FEATURE:
<223> OTHER INFORMATION: chimeric CD40-L

<400> SEQUENCE: 14

Met Ile Glu Thr Tyr Asn Gln Thr Ser Pro Arg Ser Ala Ala Thr Gly
1 5 10 15

Leu Pro Ile Ser Met Lys Ile Phe Met Tyr Leu Leu Thr Val Phe Leu
20 25 30

Ile Thr Gln Met Ile Gly Ser Ala Leu Phe Ala Val Tyr Leu His Arg
35 40 45

Arg Leu Asp Lys Ile Glu Asp Glu Arg Asn Leu His Glu Asp Phe Val
50 55 60

Phe Met Lys Thr Ile Gln Arg Cys Asn Thr Gly Glu Arg Ser Leu Ser
65 70 75 80

Leu Leu Asn Cys Glu Glu Ile Lys Ser Gln Phe Glu Gly Phe Val Lys
85 90 95

Asp Ile Met Leu Asn Lys Glu Glu Thr Lys Lys Asp Glu Asp Pro Gln
100 105 110

Ile Ala Ala His Val Val Ser Glu Ala Asn Ser Asn Ala Ala Ser Val
115 120 125

Leu Gln Trp Ala Lys Lys Gly Tyr Tyr Thr Met Lys Ser Asn Leu Val
130 135 140

Thr Leu Glu Asn Gly Lys Gln Leu Thr Val Lys Arg Gln Gly Leu Tyr
145 150 155 160

Tyr Ile Tyr Ala Gln Val Thr Phe Cys Ser Asn Arg Glu Ala Ser Ser
165 170 175

Gln Ala Pro Phe Ile Val Gly Leu Trp Leu Lys Pro Ser Ser Gly Ser
180 185 190

Glu Arg Ile Leu Leu Lys Ala Ala Asn Thr His Ser Ser Ala Lys Pro
195 200 205

Cys Gly Gln Gln Ser Ile His Leu Gly Gly Val Phe Glu Leu Gln Pro
210 215 220

Gly Ala Ser Val Phe Val Asn Val Thr Asp Pro Ser Gln Val Ser His
225 230 235 240

Gly Thr Gly Phe Thr Ser Phe Gly Leu Leu Lys Leu
245 250

<210> SEQ ID NO 15
<211> LENGTH: 260
<212> TYPE: PRT
<213> ORGANISM: Artificial sequence
<220> FEATURE:
<223> OTHER INFORMATION: chimeric CD40-L

<400> SEQUENCE: 15

Met Ile Glu Thr Tyr Ser Gln Pro Ser Pro Arg Ser Val Ala Thr Gly
1 5 10 15

Leu Pro Ala Ser Met Lys Ile Phe Met Tyr Leu Leu Thr Val Phe Leu
20 25 30

Ile Thr Gln Met Ile Gly Ser Val Leu Phe Ala Val Tyr Leu His Arg
35 40 45

Arg Leu Asp Lys Val Glu Glu Glu Val Asn Leu His Glu Asp Phe Val
50 55 60

Phe Ile Lys Lys Leu Lys Arg Cys Asn Lys Gly Glu Gly Ser Leu Ser
65 70 75 80

Leu Leu Asn Cys Glu Glu Met Arg Arg Gln Phe Glu Asp Leu Val Lys
85 90 95

Asp Ile Thr Leu Asn Lys Glu Glu Lys Lys Glu Asn Ser Phe Glu Met
100 105 110

Gln Arg Gly Asp Glu Asp Pro Gln Ile Ala Ala His Val Val Ser Glu
115 120 125

Ala Asn Ser Asn Ala Ala Ser Val Leu Gln Trp Ala Lys Lys Gly Tyr
130 135 140

Tyr Thr Met Lys Ser Asn Leu Val Thr Leu Glu Asn Gly Lys Gln Leu
145 150 155 160

Thr Val Lys Arg Gln Gly Leu Tyr Tyr Ile Tyr Ala Gln Val Thr Phe
165 170 175

Cys Ser Asn Arg Glu Pro Ser Ser Gln Arg Pro Phe Ile Val Gly Leu
180 185 190

Trp Leu Lys Pro Ser Ser Gly Ser Glu Arg Ile Leu Leu Lys Ala Ala
195 200 205

Asn Thr His Ser Ser Ser Gln Leu Cys Glu Gln Gln Ser Ile His Leu
210 215 220

Gly Gly Val Phe Glu Leu Gln Pro Gly Ala Ser Val Phe Val Asn Val
225 230 235 240

Thr Asp Pro Ser Gln Val Ser His Gly Thr Gly Phe Thr Ser Phe Gly
245 250 255

Leu Leu Lys Leu
260

<210> SEQ ID NO 16
<211> LENGTH: 252
<212> TYPE: PRT
<213> ORGANISM: Artificial sequence
<220> FEATURE:
<223> OTHER INFORMATION: chimeric CD40-L

<400> SEQUENCE: 16

Met Ile Glu Thr Tyr Asn Gln Thr Ser Pro Arg Ser Ala Ala Thr Gly
1 5 10 15

Leu Pro Ile Ser Met Lys Ile Phe Met Tyr Leu Leu Thr Val Phe Leu
20 25 30

Ile Thr Gln Met Ile Gly Ser Ala Leu Phe Ala Val Tyr Leu His Arg
35 40 45

Arg Leu Asp Lys Ile Glu Asp Glu Arg Asn Leu His Glu Asp Phe Val
50 55 60

Phe Met Lys Thr Ile Gln Arg Cys Asn Thr Gly Glu Arg Ser Leu Ser
65 70 75 80

-continued

```
Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ser Gln Leu
        195                 200                 205

Cys Glu Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 17
<211> LENGTH: 260
<212> TYPE: PRT
<213> ORGANISM: Artificial sequence
<220> FEATURE:
<223> OTHER INFORMATION: chimeric CD40-L

<400> SEQUENCE: 17

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Thr Leu Glu Asn Gly Lys Gln Leu
145                 150                 155                 160

Thr Val Lys Arg Gln Gly Leu Tyr Tyr Ile Tyr Ala Gln Val Thr Phe
                165                 170                 175

Cys Ser Asn Arg Glu Pro Ser Ser Gln Arg Pro Phe Ile Val Gly Leu
            180                 185                 190
```

-continued

```
Trp Leu Lys Pro Ser Ser Gly Ser Glu Arg Ile Leu Leu Lys Ala Ala
        195                 200                 205

Asn Thr His Ser Ser Ala Lys Pro Cys Gly Gln Gln Ser Ile His Leu
    210                 215                 220

Gly Gly Val Phe Glu Leu Gln Pro Gly Ala Ser Val Phe Val Asn Val
225                 230                 235                 240

Thr Asp Pro Ser Gln Val Ser His Gly Thr Gly Phe Thr Ser Phe Gly
                245                 250                 255

Leu Leu Lys Leu
            260


<210> SEQ ID NO 18
<211> LENGTH: 252
<212> TYPE: PRT
<213> ORGANISM: Artificial sequence
<220> FEATURE:
<223> OTHER INFORMATION: chimeric CD40-L

<400> SEQUENCE: 18

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Pro Ser Ser
                165                 170                 175

Gln Arg Pro Phe Ile Val Gly Leu Trp Leu Lys Pro Ser Ser Gly Ser
            180                 185                 190

Glu Arg Ile Leu Leu Lys Ala Ala Asn Thr His Ser Ser Ala Lys Pro
        195                 200                 205

Cys Gly Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250


<210> SEQ ID NO 19
<211> LENGTH: 783
<212> TYPE: DNA
<213> ORGANISM: Artificial sequence
<220> FEATURE:
```

-continued

<223> OTHER INFORMATION: chimeric human/mouse CD40 ligand

<400> SEQUENCE: 19
atgatagaaa catacagcca accttccccc agatccgtgg caactggact tccagcgagc 60
atgaagattt ttatgtattt acttactgtt ttccttatca cccaaatgat tggatctgtg 120
ctttttgctg tgtatcttca tagaagattg gataaggtcg aagaggaagt aaaccttcat 180
gaagattttg tattcataaa aaagctaaag agatgcaaca aaggagaagg atctttatcc 240
ttgctgaact gtgaggagat gagaaggcaa tttgaagacc ttgtcaagga tataacgtta 300
aacaaagaag agaaaaaaga aaacagcttt gaaatgcaaa gaggtgatga ggatcctcaa 360
attgcagcac acgttgtaag cgaagccaac agtaatgcag catccgttct acagtgggcc 420
aagaaaggat attataccat gaaaagcaac ttggtaaccc tggaaaatgg gaaacagctg 480
acggttaaaa gacaaggact ctattatatc tatgctcaag tcaccttctg ctctaatcgg 540
gagccttcga gtcaacgccc attcatcgtc ggcctctggc tgaagcccag cagtggatct 600
gagagaatct tactcaaggc ggcaaatacc cacagttcct cccagctttg cgagcagcag 660
tctgttcact tgggcggagt gtttgaatta caaccaggtg cttcggtgtt tgtcaatgtg 720
actgatccaa gccaagtgag ccatggcact ggcttcacgt cctttggctt actcaaactc 780
tga 783

<210> SEQ ID NO 20
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 20
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggctg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agatgaggat cctcaaattg cagcacacgt tgtaagcgaa 360
gccaacagta atgcagcatc cgttctacag tgggccaaga aaggatatta taccatgaaa 420
agcaacttgg taaccctgga aaatgggaaa cagctgacgg ttaaaagaca aggactctat 480
tatatctatg ctcaagtcac cttctgctct aatcgggagc cttcgagtca acgcccattc 540
atcgtcggcc tctggctgaa gcccagcagt ggatctgaga gaatcttact caaggcggca 600
aatacccaca gttcctccca gctttgcgag cagcagtctg ttcacttggg cggagtgttt 660
gaattacaac caggtgcttc ggtgtttgtc aatgtgactg atccaagcca agtgagccat 720
ggcactggct tcacgtcctt tggcttactc aaactctga 759

<210> SEQ ID NO 21
<211> LENGTH: 783
<212> TYPE: DNA
<213> ORGANISM: Artificial sequence
<220> FEATURE:
<223> OTHER INFORMATION: chimeric human/mouse CD40 ligand

<400> SEQUENCE: 21
atgatagaaa catacagcca accttccccc agatccgtgg caactggact tccagcgagc 60
atgaagattt ttatgtattt acttactgtt ttccttatca cccaaatgat tggatctgtg 120
ctttttgctg tgtatcttca tagaagattg gataaggtcg aagaggaagt aaaccttcat 180
gaagattttg tattcataaa aaagctaaag agatgcaaca aaggagaagg atctttatcc 240
ttgctgaact gtgaggagat gagaaggcaa tttgaagacc ttgtcaagga tataacgtta 300
aacaaagaag agaaaaaaga aaacagcttt gaaatgcaaa gaggtgatga ggatcctcaa 360
attgcagcac acgttgtaag cgaagccaac agtaatgcag catccgttct acagtgggcc 420
aagaaaggat attataccat gaaaagcaac ttggtaaccc tggaaaatgg gaaacagctg 480
acggttaaaa gacaaggact ctattatatc tatgctcaag tcaccttctg ctctaatcgg 540
gaggcttcga gtcaagcccc attcatcgtc ggcctctggc tgaagcccag cagtggatct 600
gagagaatct tactcaaggc ggcaaatacc cacagttcct cccagctttg cgagcagcag 660
tctgttcact tgggcggagt gtttgaatta caaccaggtg cttcggtgtt tgtcaatgtg 720
actgatccaa gccaagtgag ccatggcact ggcttcacgt cctttggctt actcaaactc 780
tga 783

<210> SEQ ID NO 22
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 22
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggctg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agatgaggat cctcaaattg cagcacacgt tgtaagcgaa 360
gccaacagta atgcagcatc cgttctacag tgggccaaga aaggatatta taccatgaaa 420
agcaacttgg taaccctgga aaatgggaaa cagctgacgg ttaaaagaca aggactctat 480
tatatctatg ctcaagtcac cttctgctct aatcgggagg cttcgagtca agccccattc 540
atcgtcggcc tctggctgaa gcccagcagt ggatctgaga gaatcttact caaggcggca 600
aatacccaca gttcctccca gctttgcgag cagcagtctg ttcacttggg cggagtgttt 660
gaattacaac caggtgcttc ggtgtttgtc aatgtgactg atccaagcca agtgagccat 720
ggcactggct tcacgtcctt tggcttactc aaactctga 759

<210> SEQ ID NO 23
<211> LENGTH: 783
<212> TYPE: DNA
<213> ORGANISM: Artificial sequence
<220> FEATURE:
<223> OTHER INFORMATION: chimeric human/mouse CD40 ligand -continued

<400> SEQUENCE: 23

```
atgatagaaa catacagcca accttccccc agatccgtgg caactggact tccagcgagc     60
atgaagattt ttatgtattt acttactgtt ttccttatca cccaaatgat tggatctgtg    120
ctttttgctg tgtatcttca tagaagattg gataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gaggcttcga gtcaagcccc attcatcgtc ggcctctggc tgaagcccag cagtggatct    600
gagagaatct tactcaaggc ggcaaatacc cacagttcct cccagctttg cgagcagcag    660
tctattcact tgggcggagt gtttgaatta caaccaggtg cttcggtgtt tgtcaatgtg    720
actgatccaa gccaagtgag ccatggcact ggcttcacgt cctttggctt actcaaactc    780
tga                                                                  783
```

<210> SEQ ID NO 24
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 24

```
atgatcgaaa catacaacca aacttctccc cgatctgcgg ccactggact gcccatcagc     60
atgaaaattt ttatgtattt acttactgtt tttcttatca cccagatgat tgggtcagca    120
ctttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagat taaaagccag tttgaaggct ttgtgaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta taccatgaaa    420
agcaacttgg taaccctgga aaatgggaaa cagctgacgg ttaaaagaca aggactctat    480
tatatctatg ctcaagtcac cttctgctct aatcgggagg cttcgagtca agccccattc    540
atcgtcggcc tctggctgaa gcccagcagt ggatctgaga gaatcttact caaggcggca    600
aatacccaca gttcctccca gctttgcgag cagcagtcta ttcacttggg cggagtgttt    660
gaattacaac caggtgcttc ggtgtttgtc aatgtgactg atccaagcca agtgagccat    720
ggcactggct tcacgtcctt tggcttactc aaactctga                           759
```

<210> SEQ ID NO 25
<211> LENGTH: 783
<212> TYPE: DNA
<213> ORGANISM: Artificial sequence
<220> FEATURE:
<223> OTHER INFORMATION: chimeric human/mouse CD40 ligand

<400> SEQUENCE: 25
atgatagaaa catacagcca accttccccc agatccgtgg caactggact tccagcgagc 60
atgaagattt ttatgtattt acttactgtt ttccttatca cccaaatgat tggatctgtg 120
ctttttgctg tgtatcttca tagaagattg gataaggtcg aagaggaagt aaaccttcat 180
gaagattttg tattcataaa aaagctaaag agatgcaaca aaggagaagg atctttatcc 240
ttgctgaact gtgaggagat gagaaggcaa tttgaagacc ttgtcaagga tataacgtta 300
aacaaagaag agaaaaaaga aaacagcttt gaaatgcaaa gaggtgatga ggatcctcaa 360
attgcagcac acgttgtaag cgaagccaac agtaatgcag catccgttct acagtgggcc 420
aagaaaggat attataccat gaaaagcaac ttggtaaccc tggaaaatgg gaaacagctg 480
acggttaaaa gacaaggact ctattatatc tatgctcaag tcaccttctg ctctaatcgg 540
gaggcttcga gtcaagcccc attcatcgtc ggcctctggc tgaagcccag cagtggatct 600
gagagaatct tactcaaggc ggcaaatacc cacagttccg ccaagccttg cgggcagcag 660
tctattcact tgggcggagt gtttgaatta caaccaggtg cttcgtgttt tgtcaatgtg 720
actgatccaa gccaagtgag ccatggcact ggcttcacgt cctttggctt actcaaactc 780
tga 783

<210> SEQ ID NO 26
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 26
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggctg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agatgaggat cctcaaattg cagcacacgt tgtaagcgaa 360
gccaacagta atgcagcatc cgttctacag tgggccaaga aaggatatta taccatgaaa 420
agcaacttgg taaccctgga aaatgggaaa cagctgacgg ttaaaagaca aggactctat 480
tatatctatg ctcaagtcac cttctgctct aatcgggagg cttcgagtca agccccattc 540
atcgtcggcc tctggctgaa gcccagcagt ggatctgaga gaatcttact caaggcggca 600
aatacccaca gttccgccaa gccttgcggg cagcagtcta ttcacttggg cggagtgttt 660
gaattacaac caggtgcttc ggtgtttgtc aatgtgactg atccaagcca agtgagccat 720
ggcactggct tcacgtcctt tggcttactc aaactctga 759

<210> SEQ ID NO 27
<211> LENGTH: 783
<212> TYPE: DNA
<213> ORGANISM: Artificial sequence
<220> FEATURE:
<223> OTHER INFORMATION: chimeric human/mouse CD40 ligand

<400> SEQUENCE: 27
atgatagaaa catacagcca accttccccc agatccgtgg caactggact tccagcgagc 60
atgaagattt ttatgtattt acttactgtt ttccttatca cccaaatgat tggatctgtg 120
ctttttgctg tgtatcttca tagaagattg gataaggtcg aagaggaagt aaaccttcat 180
gaagattttg tattcataaa aaagctaaag agatgcaaca aaggagaagg atctttatcc 240
ttgctgaact gtgaggagat gagaaggcaa tttgaagacc ttgtcaagga tataacgtta 300
aacaaagaag agaaaaaaga aaacagcttt gaaatgcaaa gaggtgatga ggatcctcaa 360
attgcagcac acgttgtaag cgaagccaac agtaatgcag catccgttct acagtgggcc 420
aagaaaggat attataccat gaaaagcaac ttggtaaccc tggaaaatgg gaaacagctg 480
acggttaaaa gacaaggact ctattatatc tatgctcaag tcaccttctg ctctaatcgg 540
gagccttcga gtcaacgccc attcatcgtc ggcctctggc tgaagcccag cagtggatct 600
gagagaatct tactcaaggc ggcaaatacc cacagttcct cccagctttg cgagcagcag 660
tctattcact tgggcggagt gtttgaatta caaccaggtg cttcggtgtt tgtcaatgtg 720
actgatccaa gccaagtgag ccatggcact ggcttcacgt cctttggctt actcaaactc 780
tga 783

<210> SEQ ID NO 28
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 28
atgatcgaaa catacaacca aacttctccc cgatctgcgg ccactggact gcccatcagc 60
atgaaaattt ttatgtattt acttactgtt tttcttatca cccagatgat tgggtcagca 120
ctttttgctg tgtatcttca tagaaggctg gacaagatag aagatgaaag gaatcttcat 180
gaagattttg tattcatgaa aacgatacag agatgcaaca caggagaaag atccttatcc 240
ttactgaact gtgaggagat taaaagccag tttgaaggct ttgtgaagga tataatgtta 300
aacaaagagg agacgaagaa agatgaggat cctcaaattg cagcacacgt tgtaagcgaa 360
gccaacagta atgcagcatc cgttctacag tgggccaaga aaggatatta taccatgaaa 420
agcaacttgg taaccctgga aaatgggaaa cagctgacgg ttaaaagaca aggactctat 480
tatatctatg ctcaagtcac cttctgctct aatcgggagc cttcgagtca acgcccattc 540
atcgtcggcc tctggctgaa gcccagcagt ggatctgaga gaatcttact caaggcggca 600
aatacccaca gttcctccca gctttgcgag cagcagtcta ttcacttggg cggagtgttt 660
gaattacaac caggtgcttc ggtgtttgtc aatgtgactg atccaagcca agtgagccat 720
ggcactggct tcacgtcctt tggcttactc aaactctga 759

<210> SEQ ID NO 29
<211> LENGTH: 783
<212> TYPE: DNA
<213> ORGANISM: Artificial sequence
<220> FEATURE:
<223> OTHER INFORMATION: chimeric human/mouse CD40 ligand -continued

<400> SEQUENCE: 29

```
atgatagaaa catacagcca accttccccc agatccgtgg caactggact tccagcgagc     60
atgaagattt ttatgtattt acttactgtt ttccttatca cccaaatgat tggatctgtg    120
ctttttgctg tgtatcttca tagaagattg gataaggtcg aagaggaagt aaaccttcat    180
gaagattttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aaacagcttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaaccc tggaaaatgg gaaacagctg    480
acggttaaaa gacaaggact ctattatatc tatgctcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttccg ccaagccttg cgggcagcag    660
tctattcact tgggcggagt gtttgaatta caaccaggtg cttcggtgtt tgtcaatgtg    720
actgatccaa gccaagtgag ccatggcact ggcttcacgt cctttggctt actcaaactc    780
tga                                                                  783
```

<210> SEQ ID NO 30
<211> LENGTH: 759
<212> TYPE: DNA
<213> ORGANISM: Artificial sequence
<220> FEATURE:
<223> OTHER INFORMATION: chimeric human/mouse CD40 ligand

<400> SEQUENCE: 30

```
atgatcgaaa catacaacca aacttctccc cgatctgcgg ccactggact gcccatcagc     60
atgaaaattt ttatgtattt acttactgtt tttcttatca cccagatgat tgggtcagca    120
ctttttgctg tgtatcttca tagaaggctg gacaagatag aagatgaaag gaatcttcat    180
gaagattttg tattcatgaa aacgatacag agatgcaaca caggagaaag atccttatcc    240
ttactgaact gtgaggagat taaaagccag tttgaaggct ttgtgaagga tataatgtta    300
aacaaagagg agacgaagaa agatgaggat cctcaaattg cagcacacgt tgtaagcgaa    360
gccaacagta atgcagcatc cgttctacag tgggccaaga aaggatatta taccatgaaa    420
agcaacttgg taaccctgga aaatgggaaa cagctgacgg ttaaaagaca aggactctat    480
tatatctatg ctcaagtcac cttctgctct aatcgggagc cttcgagtca acgcccattc    540
atcgtcggcc tctggctgaa gcccagcagt ggatctgaga gaatcttact caaggcggca    600
aatacccaca gttccgccaa gccttgcggg cagcagtcta ttcacttggg cggagtgttt    660
gaattacaac caggtgcttc ggtgtttgtc aatgtgactg atccaagcca agtgagccat    720
ggcactggct tcacgtcctt tggcttactc aaactctga                           759
```

UNITED STATES PATENT AND TRADEMARK OFFICE
CERTIFICATE OF CORRECTION

| | | |
|---|---|---|
| PATENT NO. | : 12,239,666 B2 | |
| APPLICATION NO. | : 17/253927 | |
| DATED | : March 4, 2025 | |
| INVENTOR(S) | : Amer A. Beg et al. | |

It is certified that error appears in the above-identified patent and that said Letters Patent is hereby corrected as shown below:

In the Specification

1. In Column 3, Line 66, delete "GRILHYLKAKEYSHCAWTIVR VEILRNFYFINRLTGYLRN" and insert -- GRILHYLKAKEYSHCAWTIVRVEILRNFYFINRLTGYLRN --, therefor.
2. In Column 17, Line 41, delete "GALS," and insert -- GAL9, --, therefor.
3. In Column 18, Line 55, delete "Ipilumumab" and insert -- Ipilimumab --, therefor.
4. In Column 18, Line 60, delete "GALS," and insert -- GAL9, --, therefor.
5. In Column 23, Line 35, delete "siiRNA," and insert -- siRNA, --, therefor.
6. In Column 23, Lines 62-63, delete "lentivrus," and insert -- lentivirus, --, therefor.

In the Claims

7. In Column 79, Line 66, in Claim 1, delete "IFN&" and insert -- IFNε --, therefor.
8. In Column 80, Line 59, in Claim 1, delete "IFN" and insert -- IFNω --, therefor.

Signed and Sealed this
Seventeenth Day of June, 2025

Coke Morgan Stewart
*Acting Director of the United States Patent and Trademark Office*